United States Patent
Matsumoto et al.

(10) Patent No.: US 11,344,488 B2
(45) Date of Patent: May 31, 2022

(54) COOL-SENSATION IMPARTER COMPOSITION CONTAINING 2,2,6-TRIMETHYLCYCLOHEXANECARBOXYLIC ACID DERIVATIVE

(71) Applicant: TAKASAGO INTERNATIONAL CORPORATION, Tokyo (JP)

(72) Inventors: Takaji Matsumoto, Kanagawa (JP); Hisanori Itoh, Kanagawa (JP); Tomoharu Sato, Tokyo (JP); Masashi Otsuka, Kanagawa (JP); Makoto Harada, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 46 days.

(21) Appl. No.: 16/756,015

(22) PCT Filed: Oct. 16, 2018

(86) PCT No.: PCT/JP2018/038425
§ 371 (c)(1),
(2) Date: Apr. 14, 2020

(87) PCT Pub. No.: WO2019/078185
PCT Pub. Date: Apr. 25, 2019

(65) Prior Publication Data
US 2020/0297607 A1  Sep. 24, 2020

(30) Foreign Application Priority Data
Oct. 16, 2017 (JP) .............................. JP2017-200504

(51) Int. Cl.
| A61K 8/42 | (2006.01) |
| A23L 27/20 | (2016.01) |
| A23G 3/36 | (2006.01) |
| A23G 4/06 | (2006.01) |
| A61Q 11/00 | (2006.01) |

(52) U.S. Cl.
CPC .............. *A61K 8/42* (2013.01); *A23G 3/36* (2013.01); *A23G 4/06* (2013.01); *A23L 27/20* (2016.08); *A61Q 11/00* (2013.01)

(58) Field of Classification Search
CPC .. A61K 8/42; A23L 27/20; A23G 3/36; A23G 4/06; A61Q 11/00
See application file for complete search history.

(56) References Cited

U.S. PATENT DOCUMENTS

| 3,988,482 A | 10/1976 | Higashiyama et al. |
| 4,038,270 A | 7/1977 | Higashiyama et al. |
| 4,230,688 A | 10/1980 | Rowsell et al. |
| 4,459,425 A | 7/1984 | Amano et al. |
| 5,288,702 A | 2/1994 | Ogura et al. |
| 5,608,119 A | 3/1997 | Amano et al. |
| 6,592,884 B2 | 7/2003 | Hofmann et al. |
| 6,780,443 B1 | 8/2004 | Nakatsu et al. |
| 7,414,152 B2 * | 8/2008 | Galopin ................. A61Q 19/00 564/189 |
| 7,482,378 B2 | 1/2009 | Erman et al. |
| RE44,339 E | 7/2013 | Galopin et al. |
| 10,494,330 B2 * | 12/2019 | Itoh ......................... C07C 69/68 |
| 2002/0042356 A1 | 4/2002 | Ujihara et al. |
| 2002/0198412 A1 | 12/2002 | Green et al. |
| 2003/0215532 A1 | 11/2003 | Nakatsu et al. |
| 2004/0052735 A1 | 3/2004 | Nakatsu et al. |
| 2004/0067970 A1 | 4/2004 | Foster et al. |

(Continued)

FOREIGN PATENT DOCUMENTS

| JP | 47-16647 A | 9/1972 |
| JP | 47-16648 A | 9/1972 |

(Continued)

OTHER PUBLICATIONS

Leffingwell (Cooling Ingredients and their mechanism of action (2009).*
Communication dated Jul. 26, 2021, from the European Patent Office in European Application No. 18867351.1.
Ken Suzuki et al., "A New Hybrid Phosphine Ligand for Palladium-Catalyzed Animation of Aryl Halides", Adv. Synth. Catal., vol. 350, Issue 5, 2008, pp. 652-656.
Makoto Tominaga et al., "Thermosensation and Pain", J. Neurobiol., vol. 61, May 28, 2004, pp. 3-12.

(Continued)

*Primary Examiner* — Shirley V Gembeh
(74) *Attorney, Agent, or Firm* — Sughrue Mion, PLLC

(57) ABSTRACT

A cooling agent composition contains a 2,2,6-trimethylcyclohexanecarboxylic acid derivative represented by the following general formula (1). The symbol * represents an asymmetric carbon atom. X represents NH, N($ZAr^2$), O or S, Z represents a single bond or an alkylene group having 1 to 3 carbon atoms which may have a substituent, $Ar^2$ represents an aryl group having 6 to 20 carbon atoms which may have a substituent or an aromatic heterocyclic group having 2 to 15 carbon atoms which may have a substituent. Y each independently represents a methylene group which may have a substituent, and n represents an integer of 0 to 3. $Ar^1$ represents an aryl group having 6 to 20 carbon atoms which may have a substituent or an aromatic heterocyclic group having 2 to 15 carbon atoms which may have a substituent.

(1)

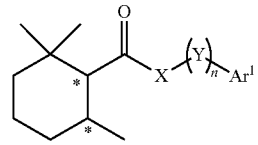

22 Claims, No Drawings

(56) References Cited

U.S. PATENT DOCUMENTS

| | | |
|---|---|---|
| 2005/0222256 A1 | 10/2005 | Erman et al. |
| 2005/0265930 A1 | 12/2005 | Erman et al. |
| 2006/0106217 A1 | 5/2006 | Foster et al. |
| 2006/0276667 A1 | 12/2006 | Galopin et al. |
| 2007/0225378 A1 | 9/2007 | Ishida et al. |
| 2008/0096969 A1 | 4/2008 | Ley |
| 2008/0142191 A1 | 6/2008 | Zwittig |
| 2008/0300314 A1 | 12/2008 | Galopin et al. |
| 2010/0056636 A1* | 3/2010 | Furrer .......... A24B 15/301 514/617 |
| 2010/0076080 A1 | 3/2010 | Yelm et al. |
| 2010/0197713 A1 | 8/2010 | Furrer et al. |
| 2011/0117147 A1 | 5/2011 | Ishida et al. |
| 2012/0263659 A1 | 10/2012 | Subkowski et al. |
| 2013/0216486 A1 | 8/2013 | Yelm et al. |
| 2013/0324557 A1 | 12/2013 | Priest et al. |
| 2014/0186272 A1 | 7/2014 | Yelm et al. |
| 2015/0086491 A1 | 3/2015 | Subkowski et al. |
| 2016/0168074 A1 | 6/2016 | Daniels et al. |
| 2016/0317532 A1 | 11/2016 | Priest et al. |
| 2017/0079304 A1 | 3/2017 | Amornrattananukool et al. |
| 2018/0093997 A1 | 4/2018 | Subkowski et al. |
| 2018/0289704 A1 | 10/2018 | Priest et al. |

FOREIGN PATENT DOCUMENTS

| | | |
|---|---|---|
| JP | 48-33069 A | 5/1973 |
| JP | 58-88334 A | 5/1983 |
| JP | 61-194049 A | 8/1986 |
| JP | 2-290827 A | 11/1990 |
| JP | 5-112494 A | 5/1993 |
| JP | 5-255186 A | 10/1993 |
| JP | 5-255217 A | 10/1993 |
| JP | 6-65023 A | 3/1994 |
| JP | 7-82200 A | 3/1995 |
| JP | 7-118119 A | 5/1995 |
| JP | 2001-294546 A | 10/2001 |
| JP | 2001-348353 A | 12/2001 |
| JP | 2002-53520 A | 2/2002 |
| JP | 2005-343915 A | 12/2005 |
| JP | 2006-512294 A | 4/2006 |
| JP | 2007-511546 A | 5/2007 |
| JP | 2007-530689 A | 11/2007 |
| JP | 2008-501017 A | 1/2008 |
| JP | 2008-115181 A | 5/2008 |
| JP | 2008-530806 A | 8/2008 |
| JP | 2009-263664 A | 11/2009 |
| JP | 2010-527943 A | 8/2010 |
| JP | 2011-530608 A | 12/2011 |
| JP | 2013-511270 A | 4/2013 |
| JP | 2014-503486 A | 2/2014 |
| JP | 2014-227390 A | 12/2014 |
| JP | 2016-532682 A | 10/2016 |
| JP | 2017-513493 A | 6/2017 |
| WO | 2007/048265 A1 | 5/2007 |
| WO | 2010/147653 A1 | 12/2010 |
| WO | 2013/033501 A1 | 3/2013 |
| WO | 2015/013184 A1 | 1/2015 |

OTHER PUBLICATIONS

Sonya Johnson et al., "Trigeminal Receptor Study of High-Intensity Cooling Agents", J. Agric. Food Chem., vol. 66, DOI: 10.1021/acs.jafc.6b04838, 2017, pp. 2319-2323.

Bernhard Neises et al., "Simple Method for the Esterification Carboxylic Acids", Angew. Chem. Int. Ed., vol. 17, 1978, pp. 522-524.

International Search Report (PCT/ISA/210) dated Dec. 25, 2018 issued by the International Searching Authority in International Application No. PCT/JP2018/038425.

Written Opinion (PCT/ISA/237) dated Dec. 25, 2018 issued by the International Searching Authority in International Application No. PCT/JP2018/038425.

* cited by examiner

COOL-SENSATION IMPARTER COMPOSITION CONTAINING 2,2,6-TRIMETHYLCYCLOHEXANECARBOXYLIC ACID DERIVATIVE

CROSS REFERENCE TO RELATED APPLICATIONS

This application is a National Stage of International Application No. PCT/JP2018/038425 filed on Oct. 16, 2018, claiming priority from Japanese Application No. 2017-200504 filed Oct. 16, 2017, the disclosures of which are incorporated herein in their entirety by reference.

TECHNICAL FIELD

The present invention relates to a cooling agent composition containing a novel 2,2,6-trimethylcyclohexanecarboxylic acid derivative. Further, the present invention relates to a sensory stimulant composition containing the cooling agent composition, a flavor or fragrance composition containing the sensory stimulant composition, a product containing the sensory stimulant composition or the flavor or fragrance composition, a method for manufacturing the product, and a novel 2,2,6-trimethylcyclohexanecarboxylic acid derivative.

BACKGROUND ART

Up to now, cooling agents which exert a refreshing sense (refresh-feeling) or cool sense (cool-feeling), namely cooling effect, on human skin, oral cavity, nose and throat are used in dentifrices, sweets (e.g., chewing gum, candy, and the like), tobacco, poultice, cosmetics, and the like. As a flavor or fragrance substance that provides such a refresh-feeling or cool-feeling, 1-menthol is now broadly used. However, the cooling effect of 1-menthol has a weak point that the cooling effect thereof lacks persistence, and the cooling effect is enhanced when the using amount thereof is increased but different stimuli such as bitterness sometimes accompanies. Furthermore, there is a problem that 1-menthol has a unique strong minty odor and high volatility.

In view of the above-described weak points of 1-menthol, synthesis of 1-menthol derivatives has been actively conducted as studies of compounds having a cooling effect in recent years. As a result, a large number of substitutes for 1-menthol have been proposed and used. Examples thereof include 3-substituted-p-menthane (e.g., see PTL 1), N-substituted-p-menthan-3-carboxamides (e.g., see PTL 2 to PTL 5), 1-menthyl glucoside (e.g., see PTL 6), 3-(1-menthoxy)propane-1,2-diol (e.g., see PTL 7), 1-menthyl-3-hydroxybutyrate (e.g., see PTL 8), 1-alkoxy-3-(1-menthoxy) propan-2-ol (e.g., see PTL 9), esters of 3-hydroxymethyl-p-menthane (e.g., see PTL 10), N-acetylglycinementhane methyl ester (e.g., see PTL 11), 1-isopulegol (e.g., see PTL 12), (2S)-3-{(1R,2S,5R)-[5-methyl-2-(1-methylethyl)cyclohexyl]oxy}-1,2-propanediol (e.g., see PTL 13), 2-hydroxymethyl menthol (e.g., see PTL 14), menthoxyalkane-1-ol (e.g., see PTL 15), (1-menthyloxyalkoxy)alkanol (e.g., see PTL 16), N-α-(menthanecarbonyl)amino acid amide (e.g., see PTL 17), menthyl ketone derivatives (e.g., see PTL 18), isopulegol derivatives (e.g., see PTL 19), menthol derivatives having a structure similar to 8,4'-oxyneolignan (e.g., see PTL 20), and the like.

Currently, many of the compounds commercialized as cooling agents are derivatives of 1-menthol.

On the other hand, compounds which are structurally different from 1-menthol and have a cooling effect have been developed. Examples thereof include N-monosubstituted acyclic carboxamides represented by N,2,3-trimethyl-2-isopropylbutanamide (e.g., see PTL 21), icilin analogs (e.g., see PTL 22), N-phenyl-N-pyridinylbenzamide and benzenesulfonamide (e.g., see PTL 23), arylcarboxamides (e.g., see PTL 24 and PTL 25), aromatic ring-containing compound groups (e.g., see PTL 26), α-keto enamine derivatives (e.g., see PTL 27), and the like. In addition, N,2,2,6-tetramethylcyclohexanecarboxamide (e.g., see PTL 28 and Non-patent literature 4) is exemplified as the compound having a cooling effect.

CITATION LIST

Patent Literature

PTL 1: JP S47-16647 A
PTL 2: JP S47-16648 A
PTL 3: JP 2007-530689 A
PTL 4: JP 2007-511546 A
PTL 5: JP 2011-530608 A
PTL 6: JP S48-33069 A
PTL 7: JP S58-88334 A
PTL 8: JP S61-194049 A
PTL 9: JP H02-290827 A
PTL 10: JP H05-255186 A
PTL 11: JP H05-255217 A
PTL 12: JP H06-65023 A
PTL 13: JP H07-82200 A
PTL 14: JP H07-118119 A
PTL 15: JP 2001-294546 A
PTL 16: JP 2005-343915 A
PTL 17: JP 2008-115181 A
PTL 18: JP 2010-527943 A
PTL 19: WO 2013/033501 A1
PTL 20: JP 2014-227390 A
PTL 21: U.S. Pat. No. 4,230,688
PTL 22: JP 2006-512294 A
PTL 23: WO 2007/048265 A1
PTL 24: JP 2008-530806 A
PTL 25: JP 2014-503486 A
PTL 26: JP 2013-511270 A
PTL 27: U.S. Pat. No. 6,592,884
PTL 28: U.S. Pat. No. 7,482,378
PTL 29: JP H05-112494 A
PTL 30: JP 2001-348353 A
PTL 31: JP 2002-53520 A

Non Patent Literature

Non-Patent Literature 1: Shuchi Kanyo Gijutsu Shu (Koryo) Daiichibu (Known/Common Technical Book (Flavor or Fragrances) Part I)" (Jan. 29, 1999, published by the Japanese Patent Office)

Non-Patent Literature 2: Adv. Synth. Catal. (2008), Vol. 350, Issue 5,652-656

Non-patent Literature 3: J. Neurobiol. (2004), Vol. 61, 3-12

Non-patent Literature 4: J. Agric. Food Chem. (2017), DOI: 10.1021/acs.jafc.6b04838

Non-patent Literature 5: Angew. Chem. Int. Ed. (1978), Vol. 17,522-524

SUMMARY OF INVENTION

Technical Problem

However, the above-mentioned common compounds having a cooling effect have a certain level of cooling effect, but are not yet sufficiently satisfactory in terms of persistence of the cooling effect or the like. In addition, a sensory stimulation effect is required to be further improved. Further, since major commercial cooling agents including N-substituted-p-menthane-carboxamides commercially known as "WS series" (e.g., see PTL 2) are derivatives of 1-menthol, the synthesis process is multi-step and complicated. Therefore, it is expensive to manufacture derivatives of 1-menthol on an industrial scale, and thus many of these compounds become relatively expensive components.

Therefore, an object of the present invention is to provide a cooling agent composition containing a novel 2,2,6-trimethylcyclohexanecarboxylic acid derivative which is a novel compound that can be used as a cooling agent or a sensory stimulant with less undesirable stimulus feeling and excellent persistence of a refresh-feeling or a cool-feeling, and has a carbon skeleton structurally different from 1-menthol as a main structure, and which may be synthesized very simply and at low cost from inexpensive raw materials.

In addition, another object of the present invention is to provide a sensory stimulant composition containing the cooling agent composition.

Further, still another object of the present invention is to provide a flavor or fragrance composition containing the sensory stimulant composition, a product containing the sensory stimulant composition or the flavor or fragrance composition, a method for manufacturing the product, and a novel 2,2,6-trimethylcyclohexanecarboxylic acid derivative.

Solution to Problem

With the aim of achieving the objects described above, the present inventors have conducted intensive studies and found that the objects can be achieved by using a novel 2,2,6-trimethylcyclohexanecarboxylic acid derivative represented by the following general formula (1), and have accomplished the present invention.

That is, the present invention relates to the following [1] to [22].

[1] A cooling agent composition comprising a 2,2,6-trimethylcyclohexanecarboxylic acid derivative represented by the following general formula (1):

[Chem. 1]

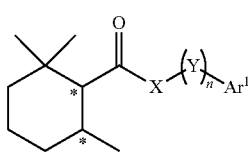

(1)

wherein the symbol * represents an asymmetric carbon atom,

X represents NH, N(ZAr$^2$), O or S, Z represents a single bond or an alkylene group having 1 to 3 carbon atoms which may have a substituent, Ar$^2$ represents an aryl group having 6 to 20 carbon atoms which may have a substituent or an aromatic heterocyclic group having 2 to 15 carbon atoms which may have a substituent, Y each independently represents a methylene group which may have a substituent, n represents an integer of 0 to 3, and Ar$^1$ represents an aryl group having 6 to 20 carbon atoms which may have a substituent or an aromatic heterocyclic group having 2 to 15 carbon atoms which may have a substituent.

[2] The cooling agent composition according to [1], wherein X represents NH or N(ZAr$^2$) in the 2,2,6-trimethylcyclohexanecarboxylic acid derivative.

[3] The cooling agent composition according to [1], wherein X represents NH or N(ZAr$^2$) in the 2,2,6-trimethylcyclohexanecarboxylic acid derivative, and the 2,2,6-trimethylcyclohexanecarboxylic acid derivative is a (1R, 6S)-form.

[4] The cooling agent composition according to [1], wherein X represents NH or N(ZAr$^2$), n represents 0 or 2, and Z represents a single bond or an ethylene group which may have a substituent in the 2,2,6-trimethylcyclohexanecarboxylic acid derivative.

[5] The cooling agent composition according to [1], wherein X represents NH or N(ZAr$^2$), n represents 0 or 2, and Z represents a single bond or an ethylene group which may have a substituent in the 2,2,6-trimethylcyclohexanecarboxylic acid derivative, and the 2,2,6-trimethylcyclohexanecarboxylic acid derivative is a (1R, 6S)-form.

[6] The cooling agent composition according to [1], wherein X represents NH or N(ZAr$^2$), n represents 2, and Z represents an ethylene group which may have a substituent, in the 2,2,6-trimethylcyclohexanecarboxylic acid derivative.

[7] The cooling agent composition according to [1], wherein X represents NH or N(ZAr$^2$), n represents 2, and Z represents an ethylene group which may have a substituent in the 2,2,6-trimethylcyclohexanecarboxylic acid derivative, and the 2,2,6-trimethylcyclohexanecarboxylic acid derivative is a (1R, 6S)-form.

[8] The cooling agent composition according to any one of [1] to [7], further comprising at least one kind of cooling substance other than the 2,2,6-trimethylcyclohexanecarboxylic acid derivative.

[9] The cooling agent composition according to [8], wherein the cooling substance is at least one cooling substance selected from the group consisting of:

one or more kinds of compounds selected from menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propane-1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, and trans-4-tert-butylcyclohexanol;

one or more kinds of sugar alcohols selected from xylitol, erythritol, dextrose, and sorbitol; and one or more kinds of natural products selected from Japanese mint oil, peppermint oil, spearmint oil, and eucalyptus oil.

[10] A sensory stimulant composition comprising the cooling agent composition according to any one of [1] to [9].

[11] The sensory stimulant composition according to [10], further comprising at least one kind of warming substance.

[12] The sensory stimulant composition according to [11], wherein the warming substance is at least one warming substance selected from the group consisting of:

one or more kinds of compounds selected from vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, bis-capsaicin, trishomocapsaicin, nomorcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more kinds of natural products selected from capsicum pepper oil, capsicum pepper oleoresin, ginger oleoresin, jambu oleoresin (extract from *Spilanthes acmella* L. var. *oleracca* Clarke), Japanese pepper extract, sanshoamide, black pepper extract, white pepper extract, and Polygonum extract.

[13] A flavor or fragrance composition comprising the sensory stimulant composition according to any one of [10] to [12].

[14] The flavor or fragrance composition according to [13], wherein a content of the sensory stimulant composition is from 0.00001 mass % to 90 mass %.

[15] A product comprising the sensory stimulant composition according to any one of [10] to [12], the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

[16] The product according to [15], wherein a content of the sensory stimulant composition is from 0.00001 mass % to 50 mass %.

[17] A product comprising the flavor or fragrance composition according to [13] or [14], the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

[18] The product according to [17], wherein a content of the flavor or fragrance composition is from 0.00001 mass % to 50 mass %.

[19] A method for manufacturing a product, comprising blending a product with the sensory stimulant composition according to any one of [10] to [12], wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

[20] A method for manufacturing a product, comprising blending a product with the flavor or fragrance composition according to [13] or [14], wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

[21] A 2,2,6-trimethylcyclohexanecarboxylic acid derivative represented by the following general formula (1-1):

[Chem. 2]

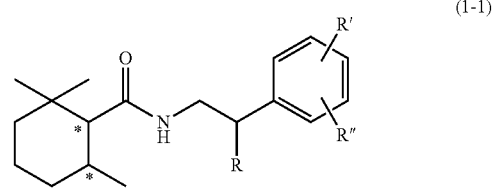

wherein the symbol * represents an asymmetric carbon atom, and R, R' and R" each independently represent a hydrogen atom, a hydroxy group, or a methoxy group.

[22] A 2,2,6-trimethylcyclohexanecarboxylic acid derivative represented by the following structural formula (10-1):

[Chem. 3]

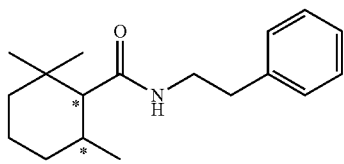

(10-1)

wherein the symbol * represents an asymmetric carbon atom.

Advantageous Effects of Invention

The present invention can provide a cooling agent composition containing a novel 2,2,6-trimethylcyclohexanecarboxylic acid derivative which can be used as a cooling agent or a sensory stimulant with less undesirable stimulus feeling and excellent persistence of a refresh-feeling or a cool-feeling, and has a carbon skeleton structurally different from 1-menthol as a main structure. The cooling agent composition of the present invention is blended with various products, so that a refresh-feeling or a cool-feeling excellent in the persistence can be imparted to these products.

Currently, most of the commercially available compounds having a cooling effect are derivatives of 1-menthol, and the derivatives of 1-menthol are relatively expensive components due to the complexity of the synthesis process thereof. However, the 2,2,6-trimethylcyclohexanecarboxylic acid derivative is a novel compound having a carbon skeleton structurally different from 1-menthol as a main structure, and can be synthesized very simply and at low cost by using citronellal as an inexpensive raw material.

In the flavor or fragrance composition including the sensory stimulant composition containing the cooling agent composition of the present invention, odorous diffusivity and lingering scent of the flavor or fragrance composition is enhanced, and a high odor quality improvement effect is also imparted to a product perfumed with the flavor or fragrance composition.

Further, the 2,2,6-trimethylcyclohexanecarboxylic acid derivative exhibits excellent characteristics that an undesirable stimulus feeling for skin is hardly given to a human body.

BRIEF DESCRIPTION OF DRAWINGS

Hereinafter, the present invention is described in detail, but the present invention is not limited to the following embodiments, and may be optionally modified and implemented without departing from the scope of the present invention. In addition, the "compound represented by the formula (X)" is sometimes simply referred to as the "compound (X)" in the present description.

"Weight %" and "mass %" have the same definition in the present description. Further, the expression "to" showing a numerical range is used to include the numerical value described therebefore as the lower limit and the numerical value described thereafter as the upper limit.

[Cooling Agent Composition]

(2,2,6-trimethylcyclohexanecarboxylic Acid Derivative Represented by Following General Formula (1))

The cooling agent composition of the present invention contains a novel 2,2,6-trimethylcyclohexanecarboxylic acid derivative represented by following general formula (1) as a cooling substance.

[Chem. 4]

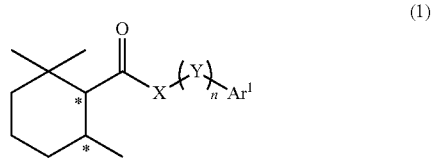

(1)

In the formula (1), a symbol * represents an asymmetric carbon atom, X represents NH, N(ZAr$^2$), O or S, Z represents a single bond or an alkylene group having 1 to 3 carbon atoms which may have a substituent, Ar$^2$ represents an aryl group having 6 to 20 carbon atoms which may have a substituent or an aromatic heterocyclic group having 2 to 15 carbon atoms which may have a substituent, Y each independently represents a methylene group which may have a substituent, n represents an integer of 0 to 3, and Ar$^1$ represents an aryl group having 6 to 20 carbon atoms which may have a substituent or an aromatic heterocyclic group having 2 to 15 carbon atoms which may have a substituent.

The 2,2,6-trimethylcyclohexanecarboxylic acid derivative represented by following general formula (1) has a cyclohexane ring structure, and has asymmetric carbons at the 1-position and 6-position as shown below.

[Chem. 5]

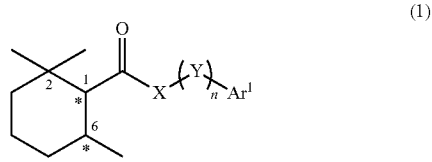

(1)

The symbol *, n, X, Y and Ar$^1$ in the above formula have the same definition as those in the formula (1).

Specifically, the 2,2,6-trimethylcyclohexanecarboxylic acid derivative represented by the general formula (1) have four kinds of diastereomers represented by the following formulas (1-a) to (1-d).

[Chem. 6]

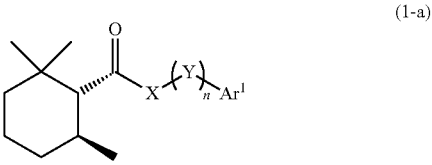

(1-a)

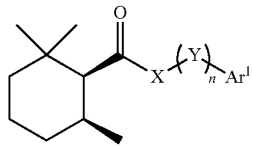

(1-b)

(1-c)

(1-d)

n, X, Y and $Ar^1$ in formulas (1-a) to (1-d) have the came definition as those in the formula (1).

The 2,2,6-trimethylcyclohexanecarboxylic acid derivative represented by the general formula (1) is preferably a trans form, and particularly preferably a (1R, 6S)-form (1-a).

Functional groups of the 2,2,6-trimethylcyclohexanecarboxylic acid derivative represented by the general formula (1) are described below.

X represents NH, $N(ZAr^2)$, O or S.

Among them, X is preferably NH or $N(ZAr^2)$ from the viewpoint of cooling intensity.

Z represents a single bond or an alkylene group having 1 to 3 carbon atoms which may have a substituent.

Examples of the alkylene group having 1 to 3 carbon atoms which may have a substituent include a methylene group, an ethylene group, and a propylene group.

Among them, Z is preferably a single bond or an ethylene group which may have a substituent, and more preferably an ethylene group which may have a substituent, from the viewpoint of cooling intensity.

Y each independently represents a methylene group which may have a substituent, and n represents an integer of 0 to 3.

Among them, n preferably represents 0 or 2, and more preferably represents 2, from the viewpoint of cooling intensity.

$Ar^1$ and $Ar^2$ each independently represent an aryl group having 6 to 20 carbon atoms which may have a substituent or an aromatic heterocyclic group having 2 to 15 carbon atoms which may have a substituent.

Examples of the aryl group having 6 to 20 carbon atoms which may have a substituent include an aromatic monocyclic group having 6 to 20 carbon atoms, an aromatic polycyclic group having 6 to 20 carbon atoms, or an aromatic fused-cyclic group having 6 to 20 carbon atoms. Specific examples thereof include a phenyl group, a naphthyl group, an anthryl group, a phenanthryl group, and an indenyl group, and a preferred specific example thereof includes a phenyl group.

Examples of the aromatic heterocyclic group having 2 to 15 carbon atoms which may have a substituent include monocyclic, polycyclic or fused aromatic heterocyclic (heteroaryl) groups such as 5- to 8-membered rings having 2 to 15 carbon atoms and containing at least 1, preferably 1 to 3 hetero elements, in which 5- or 6-membered ring is preferred. Examples of the hetero atom include a hetero element such as a nitrogen atom, an oxygen atom, and a sulfur atom.

Specific examples of the aromatic heterocyclic group having 2 to 15 carbon atoms which may have a substituent include a furyl group, a thienyl group, a pyridyl group, a pyridinyl group, a pyrazinyl group, a pyradazinyl group, a tetrazinyl group, an imidazoyl group, an oxazoyl group, a thiazoyl group, a benzofuryl group, a benzothienyl group, a quinolyl group, an isoquinolyl group, a quinoxanoyl group, a phthalazinyl group, a quinazolinyl group, a naphthyldinyl group, a cinnolinyl group, a benzimidazoline group, a benzoxazolyl group, a benzothiazolyl group, an indolyl group, and the like, and preferred specific example thereof include a thienyl group.

Examples of the substituent contained in the above alkylene group having 1 to 3 carbon atoms, the aryl group having 6 to 20 carbon atoms, and the aromatic heterocyclic group having 2 to 15 carbon atoms include an alkyl group having 1 to 6 carbon atoms such as a methyl group, an ethyl group, a n-propyl group, an isopropyl group, a n-butyl group, an isobutyl group, a sec-butyl group, a tert-butyl group, a pentyl group, and a hexyl group; a cycloalkyl group having 5 to 8 carbon atoms such as a cyclopentyl group, a cyclohexyl group, and a cycloheptyl group; a hydroxy group; a hydroxyalkyl group having 1 to 4 carbon atoms such as a hydroxymethyl group, a hydroxyethyl group, a 2-hydroxyethyl group, a 1-hydroxypropyl group, a 2-hydroxypropyl group, and a 1-hydroxybutyl group; an alkoxy group having 1 to 4 carbon atoms such as a methoxy group, an ethoxy group, a n-propoxy group, an isopropoxy group, a n-butoxy group, an isobutoxy group, a sec-butoxy group, a methylenedioxy group, and a tert-butoxy group; a mercapto group; a thioalkoxy group having 1 to 4 carbon atoms such as a thiomethoxy group, a thioethoxy group, a n-thiopropoxy group, a thioisopropoxy group, a n-thiobutoxy group, a thioisobutoxy group, a sec-thiobutoxy group, a methylenedithio group, and a tert-thiobutoxy group; halogen atoms such as fluorine atoms, chlorine atoms, bromine atoms, and iodine atoms; an aralkyl group having 7 to 12 carbon atoms such as a benzyl group, a phenylethyl group, and a naphthylmethyl group; a carbonyl group; an alkoxycarbonyl group having 2 to 8 carbon atoms such as a methoxycarbonyl group, an ethoxycarbonyl group, and a benzyloxycarbonyl group; a carboxamide group; a dialkylamino group having 2 to 8 carbon atoms such as a dimethylamino group, a diethylamino group, and a dibutylamino group; a nitrile group; a cyanoalkyl (the alkyl group having 1 to 4 carbon atoms) group such as a cyanomethyl group, a cyanoethyl group, a cyanopropyl group, and a cyanobutyl group; an aliphatic heterocyclic group such as an oxiranyl group, an aziridinyl group, a 2-oxopyropidyl group, a piperidyl group, a piperazinyl group, a morpholino group, a tetrahydrofuryl group, a tetrahydropyranyl group, and a tetrahydrothienyl group; an aromatic heterocyclic group such as a tetrazinyl group, a furyl group, a thienyl group, a pyridyl group, a pyridinyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxanoyl group, a phthalazinyl group, a quinazolinyl group, a naphthyldinyl group, a cinnolinyl group, a benzimidazoline group, a benzoxazolyl group, and a benzothiazolyl group; and the like.
(Method of Synthesizing 2,2,6-trimethylcyclohexanecarboxylic Acid Derivative Represented by General Formula (1))

The 2,2,6-trimethylcyclohexanecarboxylic acid derivative represented by the general formula (1) is synthesized by, for example, the methods represented by the following schemes 1 to 6. However, the method of synthesizing the carboxylic acid derivative is not limited to the methods of the following schemes 1 to 6.

2,2,6-trimethylcyclohexanecarboxylic acid represented by the following formula (5) (hereinafter, may be referred to as "carboxylic acid compound (5)"), which is a basic skeleton of the 2,2,6-trimethylcyclohexanecarboxylic acid derivative represented by the general formula (1), is synthesized from citronellal, 7-methoxycitronellal or 7-hydroxycitronellal, for example, according to the method shown in the following scheme 1.

In the scheme (1), a double line of a solid line and a dotted line represents a double bond or a single bond, and when the double line of the solid line and the dotted line is a single bond, $Z^1$ represents a hydroxy group or a methoxy group. In addition, Ac represents an acetyl group, and a symbol * has the same definition as those in the formula (1).

Steps [A], [B], and [C] can be performed according to the method described in PTL 29. That is, Step [A] can be performed by an enol acetylation reaction, Step [B] can be performed by a cyclization reaction with an acid catalyst, and Step [C] can be performed by an oxidation reaction.

Steps [D], [E], [F] and [G] can be performed according to the method described in PTL 30. That is, Step [D] can be performed by a grignard reaction, Step [E] can be performed by an oxidation reaction, Step [F] can be performed by an enol acetylation reaction, and Step [G] can be performed by a cyclization reaction with an acid catalyst.

In addition, Step [H] can be synthesized according to the method described in PTL 31. That is, Step [H] can be performed by nitric acid oxidation.

Among the 2,2,6-trimethylcyclohexanecarboxylic acid derivatives represented by the general formula (1), a secondary amide compound represented by the general formula (10) in which X=NH (hereinafter, may be referred to as "secondary amide compound (10)") is synthesized from the carboxylic acid compound (5), for example, according to a method shown in the following scheme 2.

[Scheme 1]

[Chem. 7]

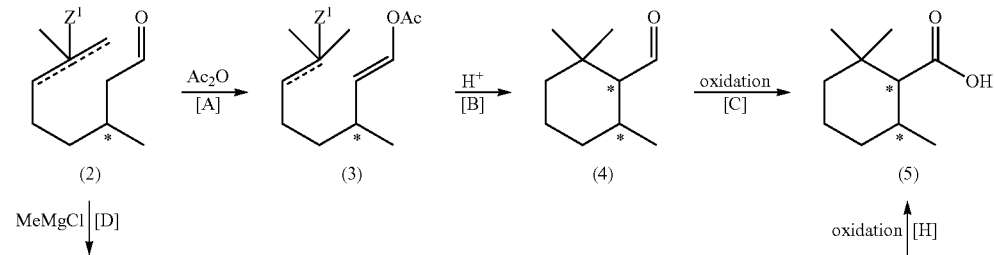

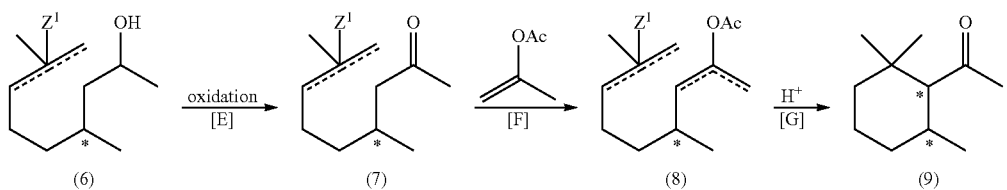

[Scheme 2]

[Chem. 8]

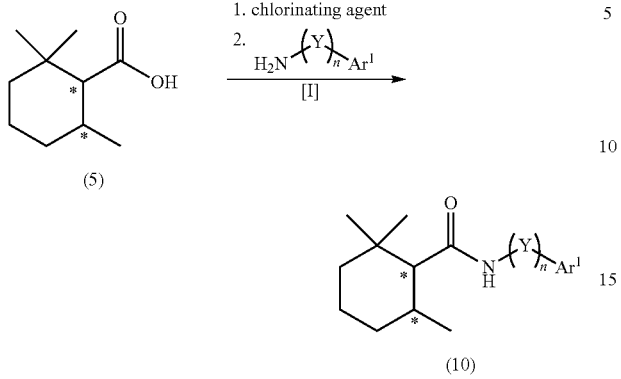

The symbol *, n, Y and Ar$^1$ in the formula of the scheme 2 have the same definition as those in the formula (1).

Step [I] can be performed according to a method similar to the method described in PTL 2 or PTL 19.

Alternatively, the secondary amide compound (10) can be synthesized from the carboxylic acid compound (5), for example, according to the method shown in the following scheme 3.

[Scheme 3]

[Chem. 9]

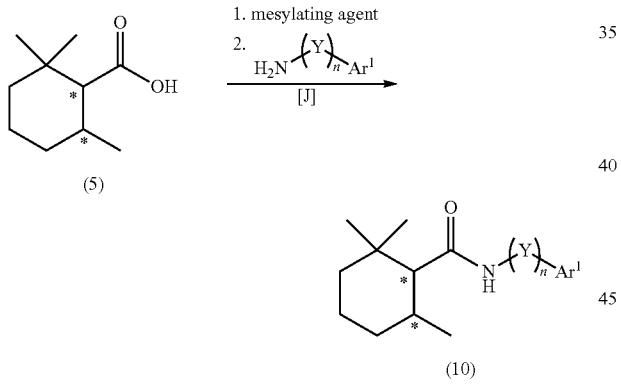

The symbol *, n, Y and Ar$^1$ in the formula of the scheme 3 have the same definition as those in the formula (1).

Step [J] can be performed by converting the carboxylic acid compound (5) into an active acyl intermediate by mesylation, and then allowing the active acyl intermediate to react with amines.

Further, among the 2,2,6-trimethylcyclohexanecarboxylic acid derivatives represented by the general formula (1), a tertiary amide compound represented by the general formula (11) in which X=N(ZAr$^2$) (hereinafter, may be referred to as "tertiary amide compound (11)") can be synthesized by reacting with the carboxylic acid compound (5) based on a method similar to Step [I] described in the scheme 2 or Step [J] described in the scheme 3 after preparing the secondary amine represented by the general formula (12), for example, according to the method of Step [K] in the following scheme 4.

[Scheme 4]

[Chem. 10]

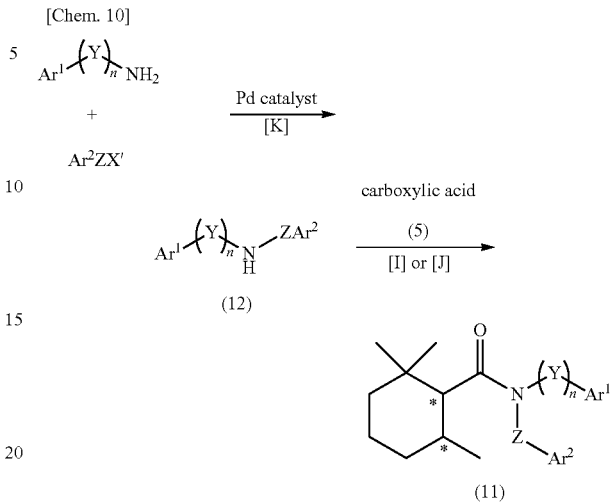

In the formula of the scheme 4, X' represents a chlorine atom, a bromine atom, or an iodine atom, and the symbol *, n, Y, Z, Ar$^1$ and Ar$^2$ have the same definition as those in the formula (1).

Step [K] can be performed according to a method similar to the method described in Non-Patent Literature 2. Steps [I] and [J] can be performed according to the method described above.

Among the 2,2,6-trimethylcyclohexanecarboxylic acid derivatives represented by the general formula (1), a carboxylic acid ester compound represented by the general formula (13) in which X=O (hereinafter, may be referred to as "ester compound (13)") is synthesized from the carboxylic acid compound (5), for example, according to the method shown in the following scheme 5.

[Scheme 5]

[Chem. 11]

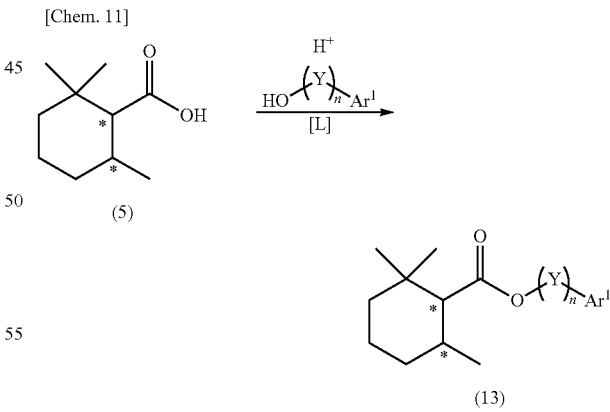

The symbol *, n, Y and Ar$^1$ in the formula of the scheme 5 have the same definition as those in the formula (1).

Step [L] can be performed according to a method similar to the method described in PTL 29.

Among the 2,2,6-trimethylcyclohexanecarboxylic acid derivatives represented by the general formula (1), a carboxylic acid thioester compound represented by the general formula (14) in which X=S (hereinafter, may be referred to as "thioester compound (14)") is synthesized from the carboxylic acid compound (5), for example, according to the method shown in the following scheme 6.

[Scheme 6]

[Chem. 12]

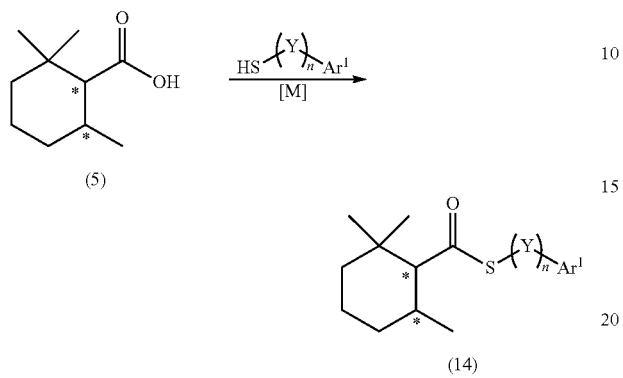

(5)

(14)

The symbol *, n, Y and Ar¹ in the formula of the scheme 6 have the same definition as those in the formula (1).

Step [M] can be performed according to a method similar to the method described in Non-Patent Literature 5. That is, Step [M] can be performed by condensation reaction.

Preferred specific examples of the 2,2,6-trimethylcyclohexanecarboxylic acid derivative represented by the general formula (1) include the secondary amide compound (10), the tertiary amide compound (11), the ester compound (13), and the thioester compound (14), but the 2,2,6-trimethylcyclohexanecarboxylic acid derivative is not limited to these compounds.

In addition, preferred specific examples of the secondary amide compound (10) include the following compounds, but the secondary amide compound (10) is not limited to these examples.

In the following compounds, Me represents a methyl group, and the symbol * represents an asymmetric carbon.

[Chem. 13]

(10-1)
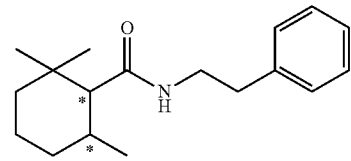

(10-2)
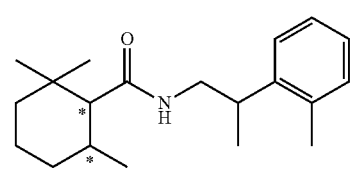

(10-3)
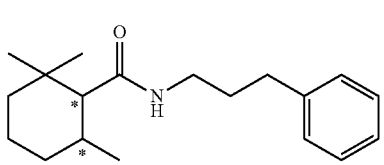

(10-4)
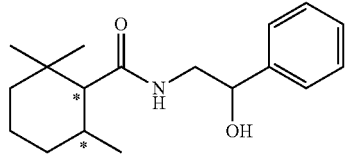

(10-5)
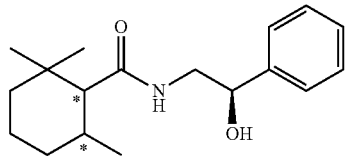

(10-6)
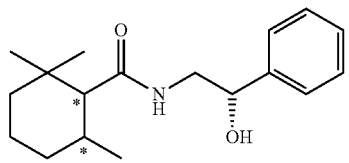

(10-7)
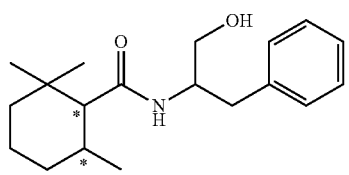

(10-8)
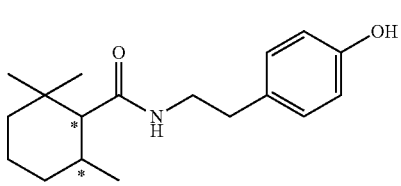

(10-9)
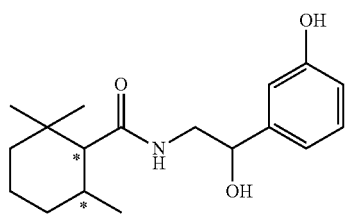

[Chem. 14]

(10-10)
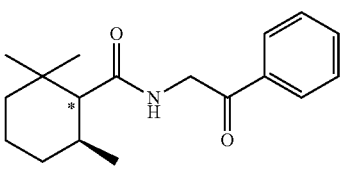

(10-11)
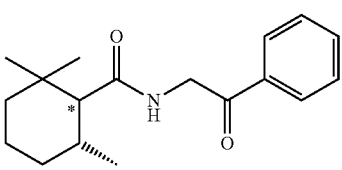

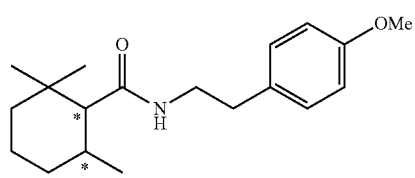 (10-12)
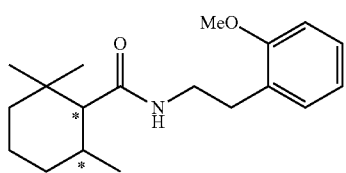 (10-13)
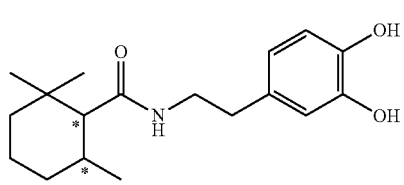 (10-14)
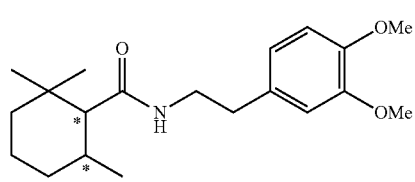 (10-15)
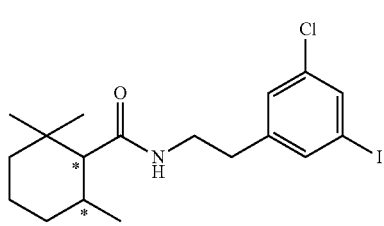 (10-16)
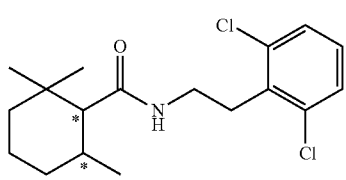 (10-17)
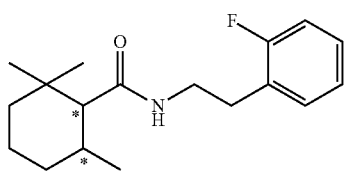 (10-18)
[Chem. 15]
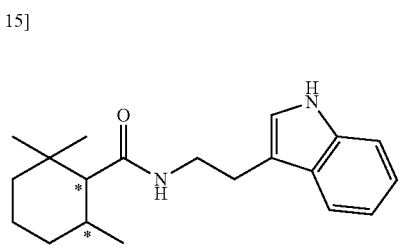 (10-19)
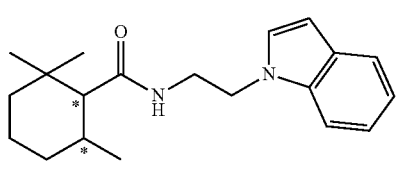 (10-20)
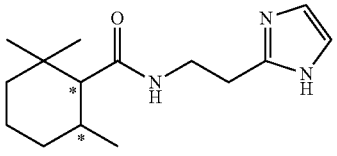 (10-21)
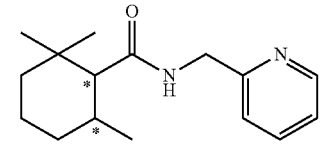 (10-22)
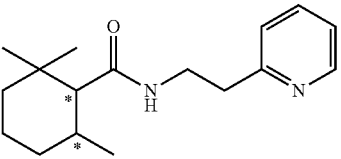 (10-23)
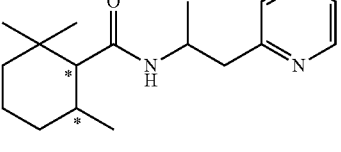 (10-24)
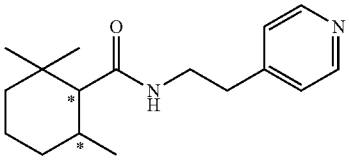 (10-25)
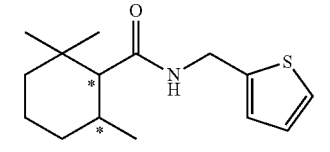 (10-26)
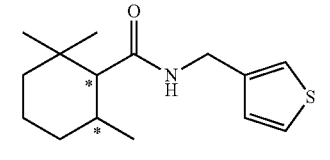 (10-27)
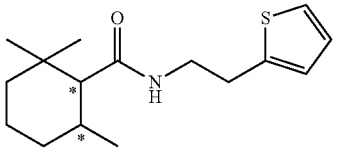 (10-28)

[Chem. 16]
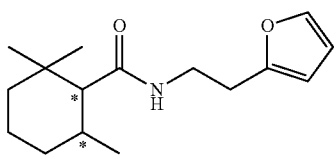 (10-29)
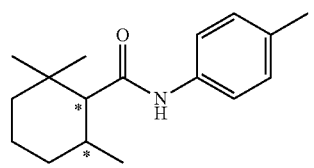 (10-30)
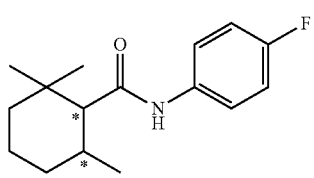 (10-31)
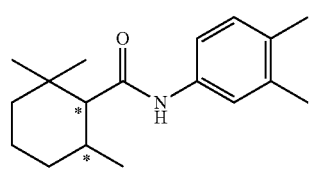 (10-32)
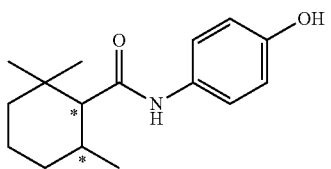 (10-33)
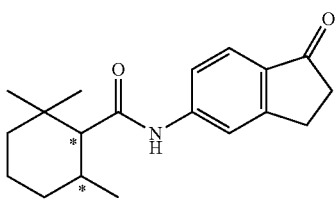 (10-34)
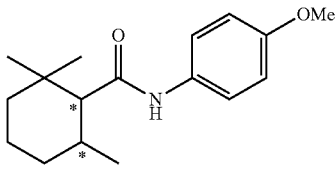 (10-35)
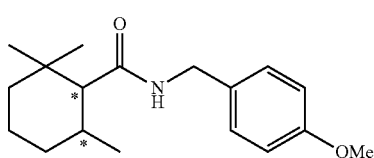 (10-36)
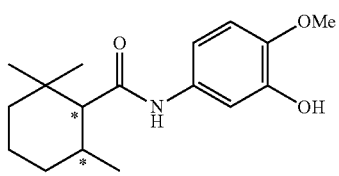 (10-37)
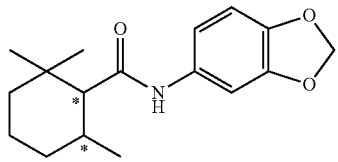 (10-38)
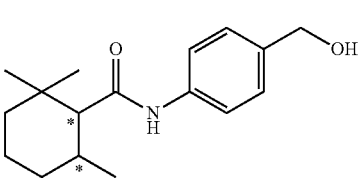 (10-39)
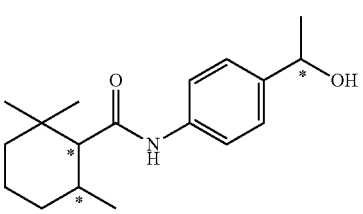 (10-40)
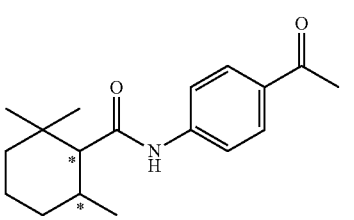 (10-41)
[Chem. 17]
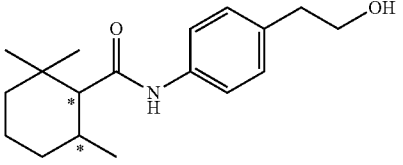 (10-42)
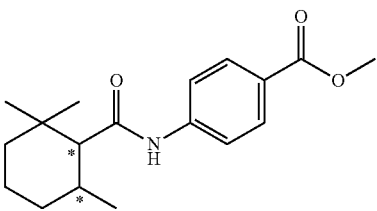 (10-43)

-continued
(10-44) 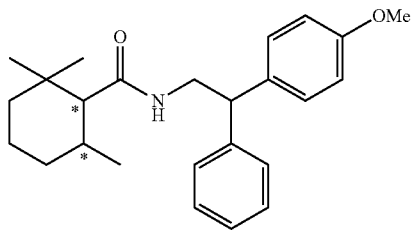
(10-45) 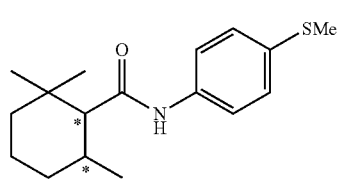
(10-46) 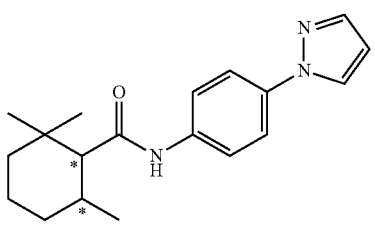
(10-47) 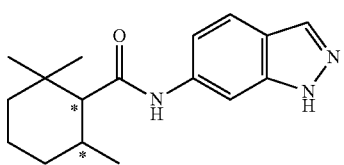
(10-48) 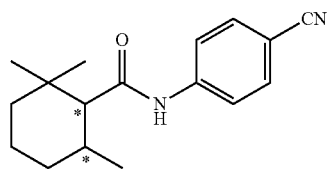
(10-49) 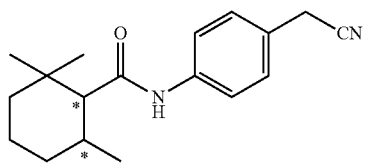
(10-50) 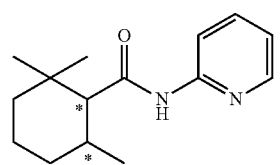
(10-51) 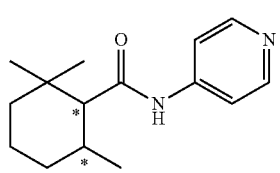
Preferred specific examples of the tertiary amide compound (11) include the following compounds, but the tertiary amide compound (11) is not limited to these examples.
In the following compounds, Me represents a methyl group, and the symbol * represents an asymmetric carbon.
[Chem. 18]
(11-1) 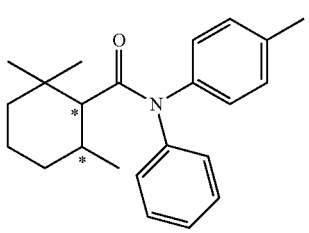
(11-2) 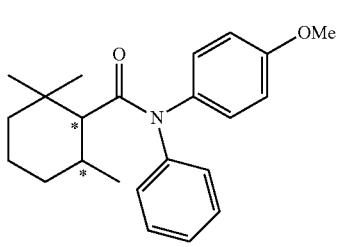
(11-3) 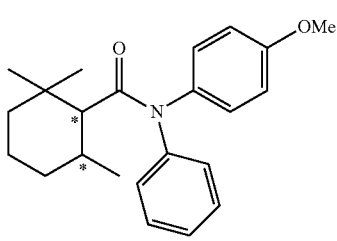
(11-4) 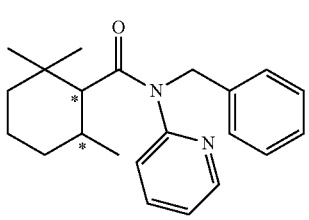
(11-5) 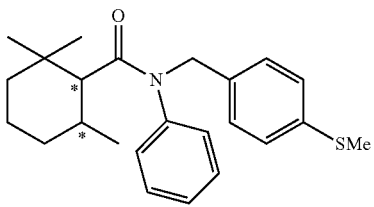
(11-6) 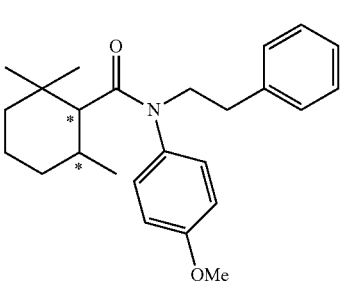

-continued

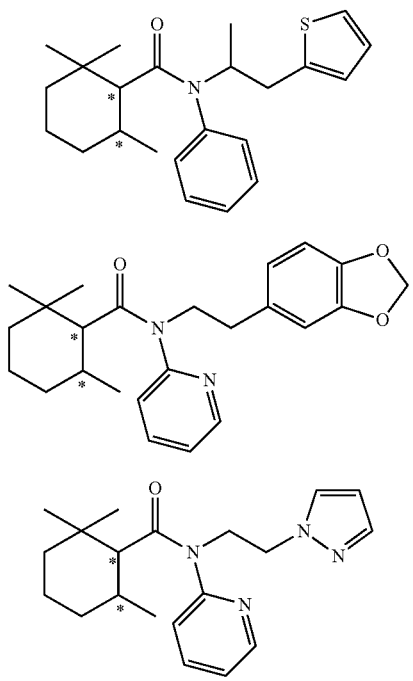

(11-7)

(11-8)

(11-9)

Preferred specific examples of the ester compound (13) include the following compounds, but the ester compound (13) is not limited to these examples.

In the following compounds, Me represents a methyl group, and the symbol * represents an asymmetric carbon.

[Chem. 19]

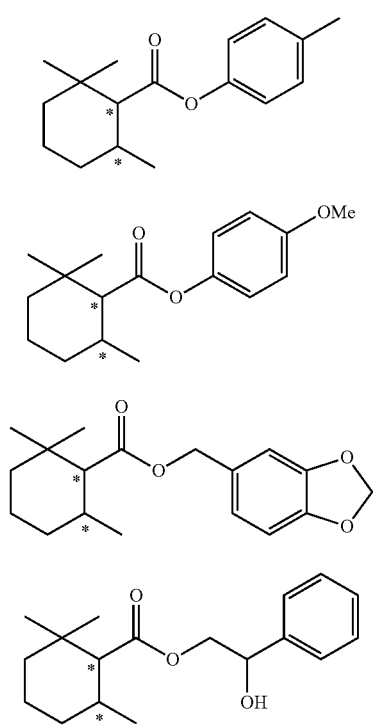

(13-1)

(13-2)

(13-3)

(13-4)

-continued

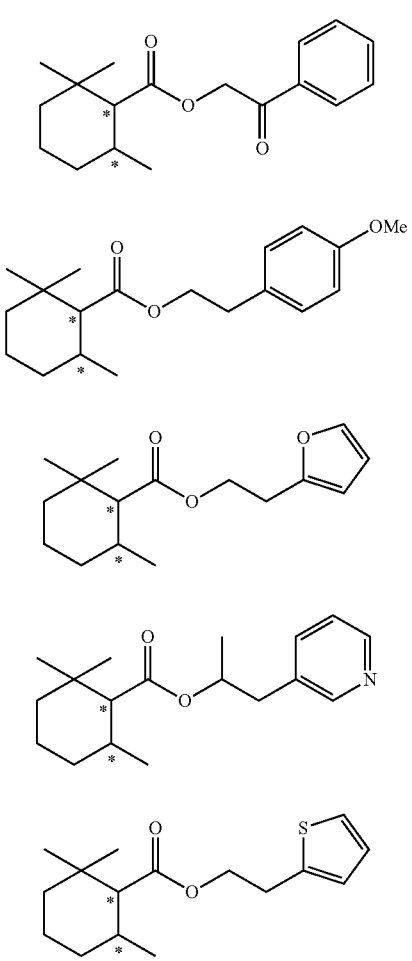

(13-5)

(13-6)

(13-7)

(13-8)

(13-9)

Preferred specific examples of the thioester compound (14) include the following compounds, but the thioester compound (14) is not limited to these examples.

In the following compounds, Me represents a methyl group, and the symbol * represents an asymmetric carbon.

[Chem. 20]

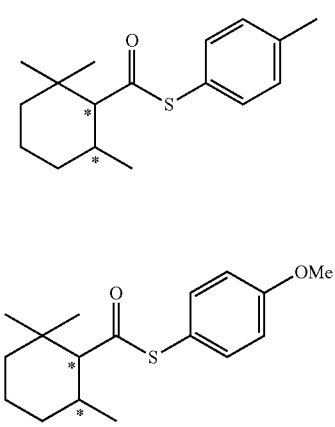

(14-1)

(14-2)

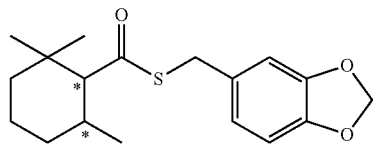 (14-3)

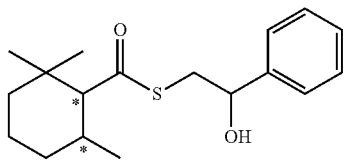 (14-4)

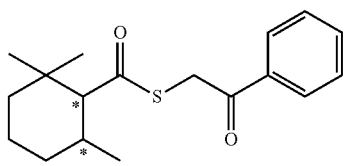 (14-5)

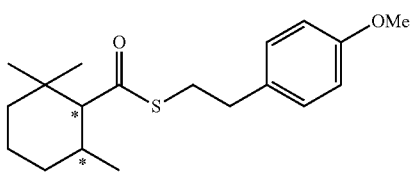 (14-6)

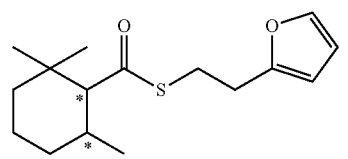 (14-7)

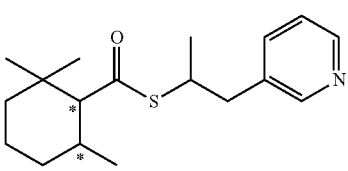 (14-8)

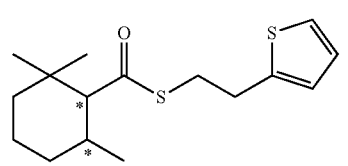 (14-9)

In addition, the 2,2,6-trimethylcyclohexanecarboxylic acid derivative represented by the general formula (1) is preferably a 2,2,6-trimethylcyclohexanecarboxylic acid derivative represented by the following general formula (1-1), from the viewpoint of cooling intensity.

[Chem. 21]

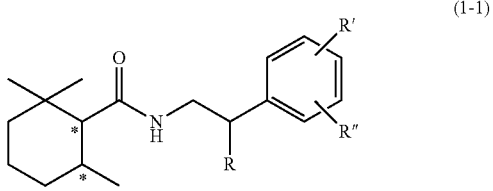 (1-1)

In the formula (1-1), a symbol * represents an asymmetric carbon atom, and R, R' and R" each independently represent a hydrogen atom, a hydroxy group, or a methoxy group.

It is preferable that R, R' and R" each independently represent a hydrogen atom or a hydroxy group from the viewpoint of cooling intensity.

The 2,2,6-trimethylcyclohexanecarboxylic acid derivative represented by the general formula (1) obtained in this way has a strong and persistent cooling effect, and can also be used alone as a cooling agent or a sensory stimulant.

The 2,2,6-trimethylcyclohexanecarboxylic acid derivative represented by the general formula (1) can also be incorporated into various products. In that case, an application range and an application method of the 2,2,6-trimethylcyclohexanecarboxylic acid derivative are required to be appropriately changed depending on kinds of products and application purposes, and the carboxylic acid derivative may be used in a concentration of generally 0.00001 mass % to 50 mass %, preferably 0.0001 mass % to 20 mass %, and particularly preferably 0.001 mass % to 5 mass %, based on the total composition of the product.

A content of the 2,2,6-trimethylcyclohexanecarboxylic acid derivative represented by the general formula (1) in the cooling agent composition of the present invention is required to be changed appropriately depending on application purpose of the cooling agent composition, and is generally 0.00001 mass % to 50 mass %, preferably 0.0001 mass % to 20 mass %, and particularly preferably 0.001 mass % to 5 mass %.

The cooling agent composition of the present invention further contains at least one kind of cooling substance other than the 2,2,6-trimethylcyclohexanecarboxylic acid derivative represented by the general formula (1), so that a cooling agent composition having an increased cooling intensity can be obtained. Further, a sensory stimulant composition containing the cooling agent composition with an increased cooling intensity can be prepared.

Examples of the cooling substance other than the 2,2,6-trimethylcyclohexanecarboxylic acid derivative represented by the above general formula (1) include:

compounds (α) such as menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propane1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]

glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, and trans-4-tert-butylcyclohexanol, and racemic and optically active forms thereof;

sugar alcohols (β) such as xylitol, erythritol, dextrose, and sorbitol;

natural products (γ) such as Japanese mint oil, peppermint oil, spearmint oil, and eucalyptus oil; and compounds (δ) described in JP 2001-294546 A, JP 2005-343915 A, JP 2007-002005 A, JP 2009-263664 A, JP 2010-254621 A, JP 2010-254622 A, JP 2011-079953 A, U.S. Pat. Nos. 4,136,163 A, 4,150,052 A, 4,178,459 A, 4,190,643 A, 4,193,936 A, 4,226,988 A, 4,230,688 A, 4,032,661 A, 4,153,679 A, 4,296,255 A, 4,459,425 A, 5,009,893 A, 5,266,592 A, 5,698,181 A, 5,725,865 A, 5,843,466 A, 6,231,900 B1, 6,277,385 B1, 6,280,762 B1, 6,306,429 B1, 6,432,441 B1, 6,455,080 B1, 6,627,233 B1, 7,078,066 B2, 6,783,783 B2, 6,884,906 B2, 7,030,273 B1, 7,090,832 B2, US 2004/0175489 A1, US 2004/0191402 A1, US 2005/0019445 A1, US 2005/0222256 A1, US 2005/0265930 A1, US 2006/015819 A1, US 2006/0249167 A1, EP 1689256 A1, WO 2005/082154 A1, WO 2005/099473 A1, WO 2006/058600 A1, WO 2006/092076 A1, and WO 2006/125334 A1;

and the like.

These may be used alone or by blending two or more of them appropriatly. It is preferable that the above cooling agent composition contains at least one cooling substance selected from the group consisting of the compounds (α), the sugar alcohols (β), and the natural products (γ), among the above compounds.

In the cooling agent composition of the present invention, the 2,2,6-trimethylcyclohexanecarboxylic acid derivative represented by the general formula (1) and the cooling substance other than the carboxylic acid derivative may be used at any ratio within a range that does not impair the effects of the present invention, and a preferred use ratio of the carboxylic acid derivative and the cooling substance other than the carboxylic acid derivative is in the range of 1:99 to 90:10 in terms of mass ratio.

The cooling agent composition of the present invention may be blended with a flavor or fragrance composition, or products such as drinks, foods, fragrances or cosmetics, toiletry products, air care products, daily necessities and household goods, oral compositions, hair care products, skin care products, body care products, detergents for clothes, soft finishing agents for clothes, quasi-drugs, and pharmaceuticals.

[Sensory Stimulant Composition]

The cooling agent composition of the present invention has a strong and persistent cooling effect, and therefore, a sensory stimulant composition of the present invention having a cooling effect can be prepared by incorporating the cooling agent composition thereto.

In the case of preparing the sensory stimulant composition of the present invention, the application range and the application method of the blending amount of the cooling agent composition are required to be appropriately changed depending on the kinds of products and application purposes. The blending amount thereof is generally from 0.00001 mass % to 50 mass %, preferably from 0.0001 mass % to 20 mass %, and particularly preferably from 0.001 mass % to 4 mass %, based on the total composition of the sensory stimulant composition.

The sensory stimulant composition of the present invention is a composition that imparts an effect of stimulating sensation. Examples of the effect of stimulating the sensation include a cooling effect and/or a warming effect. Accordingly, in the present invention, the sensory stimulant composition is described as a concept including a cooling agent composition and/or a warming agent composition.

The sensory stimulant composition of the present invention further contains at least one kind of warming substance, so that the stimulation effect of the sensory stimulant composition can be adjusted.

Examples of the warming substance include:

compounds (ε) such as vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, bis-capsaicin, trishomocapsaicin, nomorcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon, and racemic and optically active forms thereof;

natural products (ζ) such as capsicum pepper oil, capsicum pepper oleoresin, ginger oleoresin, jambu oleoresin (extract from *Spilanthes acmella* L. var. *oleracea* Clarke), Japanese pepper extract, sanshoamide, black pepper extract, white pepper extract, and Polygonum extract; and compounds (η) described in JP H08-225564 A, JP 2007-015953 A, JP 2007-510634 A, JP 2008-505868 A, WO 2007/013811 A1, WO 2003/106404 A1, EP 1323356 A2, DE 10351422 A1, US 2005/0181022 A1, and US 2008/0038386 A1; and the like.

These may be used alone or by blending two or more of them appropriately. It is preferable that the warming substance contains at least one warming substance selected from the group consisting of the compounds (ε) and the natural products (ζ), among the above compounds.

In a case where a cooling effect is aimed, the blending ratio of the warming substance to the cooling agent composition in the sensory stimulant composition of the present invention may be within a range at which the warming effect is not imparted by blending the warming substance. At this time, the blending amount of the warming substance is generally 0.001 to 0.95 times, preferably 0.01 to 0.5 times the total mass of the cooling agent composition. In the sensory stimulant composition of the present invention, the warming substance is added to the cooling agent composition at the above ratio, so that further improvement of the cooling effect can be achieved.

In a case where a warming effect is aimed, the blending ratio of the warming substance to the cooling agent composition may be within a range at which the cooling effect is not imparted by blending the cooling agent composition. At this time, the blending amount of the cooling agent composition is generally 0.001 to 0.95 times, preferably 0.01 to 0.5 times the total mass of the warming substance.

[Flavor or Fragrance Composition]

The flavor or fragrance composition of the present invention contains the sensory stimulant composition of the present invention. In addition, the flavor or fragrance composition of the present invention can contain flavor or fragrance components.

Examples of the flavor or fragrance components include various synthetic aromachemical, natural essential oil, synthetic essential oil, citrus oil, animal aromachemical and the like, and a broad range of flavor or fragrance components described in, for example, Non-Patent Literature 1 may be used.

Examples of typical ones among them include α-pinene, limonene, cis-3-hexenol, phenylethyl alcohol, styrallyl acetate, eugenol, rose oxide, linalool, benzaldehyde, muscone, Musk T (manufactured by Takasago International Corporation), Thesaron (manufactured by Takasago International Corporation), and the like.

The content of the sensory stimulant composition of the present invention can be adjusted by kinds of flavors or fragrances blended together or other components blended together, application purpose of the flavor or fragrance composition, and is preferably 0.00001 mass % to 90 mass %, more preferably 0.0001 mass % to 20 mass %, and still more preferably 0.001 mass % to 4 mass %, based on the total mass of the flavor or fragrance composition, from the viewpoint of cooling intensity.

When the flavor or fragrance composition of the present invention is used for fragrances or cosmetics, the content of the sensory stimulant composition of the present invention is generally 0.00001 mass % to 50 mass %, preferably 0.001 mass % to 50 mass %, and particularly preferably 0.01 mass % to 20 mass % based on the total mass of the flavor or fragrance composition.

When the flavor or fragrance composition of the present invention is used for drinks or foods, the content of the sensory stimulant composition of the present invention is preferably 0.0001 mass % to 50 mass %, and more preferably 0.001 mass % to 30 mass % based on the total mass of the flavor or fragrance composition.

The flavor or fragrance composition of the present invention may contain other odor retention agents commonly used in flavor or fragrance composition as necessary. Examples of other odor retention agents in that case include ethylene glycol, propylene glycol, dipropylene glycol, glycerin, hexyl glycol, benzyl benzoate, triethyl citrate, diethyl phthalate, herkorin, medium chain fatty acid triglyceride, medium chain fatty acid diglyceride, and the like, and one or two or more thereof may be contained.

[Product]

The product of the present invention contains the sensory stimulant composition of the present invention or the flavor or fragrance composition of the present invention in order to impart the cool-feeling or the sensory stimulation.

The above product is not particularly limited, and examples thereof include: drinks; foods; toiletry products such as cleaning agents, detergents for kitchen, and bleaching agents; air care products such as deodorants and aromatics; oral compositions; fragrances or cosmetics such as fragrance products, foundation cosmetics, finishing cosmetics, hair cosmetics, suntan cosmetics, and medicated cosmetics; hair care products; skin care products such as soaps; body care products such as body washers; bathing agents; cleaning agents for clothes; soft finishing agents for clothes; aerosol agents; daily necessities and household goods; and quasi-drugs and pharmaceuticals.

As the drinks, examples thereof include drinks such as fruit juice drinks, fruit wines, milk drinks, carbonated drinks, soft drinks, and health drinks; tea drinks or luxury drinks such as green tea, Oolong tea, black tea, persimmon leaf tea, chamomile tea, low striped bamboo tea, mulberry tea, dokudami tea, Pu-er tea, mate tea, Rooibos tea, Gymnema tea, Guava tea, coffee, and cocoa; soups such as Japanese style soup, Western style soup and Chinese soup; various instant drink, and the like;

as the foods, examples thereof include ices such as ice creams, sherbets and ice candies; desserts such as jelly and pudding; western style confections such as cakes, cookies, chocolates and chewing gum, Japanese style confections such as bean-jam bun, sweet bean jelly and uiro; jams; candies; breads; flavor seasoning; various instant food; various snack food, and the like;

as the oral compositions, examples thereof include dentifrice, oral cavity cleaner, mouth wash, troche, chewing gum, and the like;

as the fragrance products, examples thereof include perfume, eau de parfum, eau de toilette, eau de cologne, and the like;

as the foundation cosmetics, examples thereof include facial wash creams, vanishing creams, cleansing creams, cold creams, massage creams, milky lotions, skin lotions, beauty lotions, facial packs, makeup removers, and the like;

as the finishing cosmetics, examples thereof include foundations, face powders, solid face powders, talcum powders, rouges, lip balms, cheek rouges, eye liners, mascara, eye shadows, eyebrow pencils, eye packs, nail enamels, enamel removers, and the like;

as the hair cosmetics, examples thereof include pomade, brilliantine, hair set lotions, hair sticks, hair solids, hair oils, hair treatments, hair creams, hair tonics, hair liquids, hair sprays, bandolines, revitalizing hair tonics, hair dyes, and the like;

as the suntan cosmetics, examples thereof include suntan products, sun-screen products, and the like;

as the medicated cosmetics, examples thereof include antiperspirants, after-shaving lotions or gels, permanent wave agents, medicated soaps, medicated shampoos, medicated skin cosmetics, and the like;

as the hair care products, examples thereof include shampoos, rinses, rinse-in-shampoos, conditioners, treatments, hair packs and the like;

as the soap, examples thereof include toilet soaps, bath soaps, perfume soaps, transparent soaps, synthetic soaps, and the like;

as the body washers, examples thereof include body soaps, body shampoos, hand soaps, face creams, and the like;

as the bath agents, examples thereof include bathing agents (such as bath salts, bath tablets, and bath liquids), foam bath (such as bubble bath), bath oils (such as bath perfumes, and bath capsules), milk-baths, bath jelly, bath cubes, and the like;

as the detergents for clothes, examples thereof include heavy detergents for clothes, light detergents for clothes, liquid detergents, washing soaps, compact detergents, powder soaps, and the like;

as the soft finishing agents for clothes, examples thereof include softener, furniture carc, and the like;

as the cleaners, examples thereof include cleansers, house cleaners, toilet cleaners, bath cleaners, glass cleaners, mildew removers, cleaners for drainpipe use, and the like;

as the kitchen cleaners, examples thereof include kitchen soaps, kitchen synthetic soaps, tableware cleaners, and the like;

as the bleaching agents, examples thereof include oxidation type bleaching agents (such as chlorine type bleaching agents, and oxygen type bleaching agents), reduction type bleaching agents (such as sulfur type bleaching agents), optical bleaching agents, and the like;

as the aerosol agents, examples thereof include spray type ones, powder sprays, and the like;

as the deodorants or aromatics, examples thereof include solid type ones, gel type ones, liquid type ones (aqueous or oily), and the like;

as the daily necessities and household goods, examples thereof include tissue papers, toilet papers, and the like;

as the quasi-drugs, examples thereof include liquid bath additives, mouthwashes, and repellents such as mist spray type ones and aqueous liquid type ones; and as the pharmaceuticals, examples thereof include medicinal cosmetics, medicinal lotions, and the like.

The form of the sensory stimulant composition or the flavor or fragrance composition when the product of the present invention contains the sensory stimulant composition of the present invention or the flavor or fragrance composition of the present invention may be the form of the sensory stimulant composition itself or flavor or fragrance composition itself or another form.

As another form, examples thereof include:

a liquid form obtained by dissolving in alcohols, polyhydric alcohols such as propylene glycol, glycerin, and dipropylene glycol, or esters such as triethyl citrate, benzyl benzoate, and diethyl phthalate;

an emulsified form obtained by emulsifying with an emulsifier such as a glycerin fatty acid ester or a sucrose fatty acid ester;

a powder form obtained by coating with an excipient such as natural gums such as gum Arabic, and tragacanth gum, gelatin, and dextrin;

a solubilized form or dispersed form obtained by solubilizing or dispersing by using a surfactant such as a nonionic surfactant, an anionic surfactant, a cationic surfactant, or an amphoteric surfactant; and a microcapsule obtained by treating with an encapsulating agent, and any form may be selected and used depending on the purpose.

As a method of imparting the cool-feeling or the sensory stimulation to various products as described above by using the sensory stimulant composition of the present invention or the flavor or fragrance composition of the present invention, examples thereof include the following methods: depending on the kinds of the product to which the cool-feeling or the sensory stimulation is imparted or the final form of the product (for example, the form of the product such as a liquid form, a solid form, a powder form, a gel form, a mist form, or an aerosol form), the sensory stimulant composition or the flavor or fragrance composition may be added or applied directly to the product;

the sensory stimulant composition or the flavor or fragrance composition may be dissolved in, for example, an alcohol or a polyhydric alcohol such as propylene glycol or glycerin to form a liquid form, and then, it may be added or applied to the product;

the above composition may be formed into a solubilized form or a dispersed form by being solubilized or emulsification-dispersed by using natural gum such as gum Arabic or tragant gum or a surfactant (e.g. a nonionic surfactant such as a glycerinfatty acid ester and a sucrose fatty acid ester, an anionic surfactant, a cationic surfactant, or an amphoteric surfactant), and then, they may be added or applied to the product;

the above composition may be formed into a powder form obtained by coating with an excipient such as natural gum such as gum Arabic and tragacanth gum, gelatin, or dextrin, and then, it may be added or applied to the product; and the above composition may be formed into a microcapsule by a treatment with an encapsulating agent, and then, it may be added or applied to the product.

Further, the sensory stimulant composition or the flavor or fragrance composition may be included in an inclusion agent such as cyclodextrin so as to stabilize the composition and also make it sustained-releasable, and then may be used.

The amount of adding or applying the sensory stimulant composition or the flavor or fragrance composition to the product for imparting the cool-feeling or the sensory stimulation, can be adjusted depending on the kind or form of the product, effects or actions of imparting the cool-feeling or the sensory stimulation required for the product, or the like. In general, the amount of adding or applying the sensory stimulant composition or the flavor or fragrance composition, relative to the mass of the product, is preferably 0.00001 mass % to 50 mass %, more preferably 0.0001 mass % to 20 mass %, and still more preferably 0.001 mass % to 4 mass %, from the viewpoint of the cooling intensity.

EXAMPLES

Hereinafter, Examples and Synthetic Examples are described, but the present invention is not limited to these Examples and Synthesis Examples. The optical purity of each citronellal as a raw material used for synthesis of the carboxylic acid compound (5) is as follows.

l-citronellal: 96.6% e.e.

d-citronellal: 97.8% e.e.

An isomer ratio of a trans form (hereinafter, may be referred to as "(1R, 6S)-5") of the optically active carboxylic acid compound (5) synthesized according to the method described in PTL 29 to a cis form (hereinafter, may be referred to as "(1R, 6R)-5"), and optical purity are as follows.

[a] Carboxylic acid compound (5) derived from 1-citronellal
  Trans/cis ratio (1R, 6S)-5/(1R, 6R)-5=90/10
  Optical purity (1R, 6S)-5: 93.1% e.e.
  (1R, 6R)-5: >99.0% e.e.
[b] Carboxylic acid compound (5) derived from d-citronellal
  Trans/cis ratio (1S, 6R)-5/(1S, 6S)-5=91/9
  Optical purity (1S, 6R)-5: 96.3% e.e.
  (1S, 6S)-5: >99.0% e.e.
  Therefore, the compounds in the Examples contain minor or very small amount of diastereomers and enantiomers.

The measurement of products in Synthesis Examples and Examples was performed by using the following apparatuses and devices.

Nuclear Magnetic Resonance Spectrum: $^1$H-NMR: AM-500 (500 MHz) (manufactured by Bruker Co., Ltd.)
  External Standard Substance: tetramethylsilane
  Gas Chromatograph (GC): GC-2010AF (manufactured by Shimadzu Corporation), GC-4000Plus (manufactured by GL Sciences Inc.)
  Column: DB-WAX (30 m×0.32 nm×0.5 μm) (manufactured by Hewlett-Packard Company), IC-1 (30 m×0.25 mm×0.25 μm) (manufactured by Hewlett-Packard Company), Rtx-1 (30 m×0.25 mm×0.25 μm) (manufactured by ReStek, Inc.), Inert Cap1 (30 m×0.25 mm×0.25 μm) (manufactured by GL Sciences Inc.)
  High-Resolution Mass Spectrum (FIRMS): JMS-T100GCV (manufactured by JEOL Ltd.)
  Melting point: melting point measurement device (serial No.: 2678) (manufactured by Yanagimoto Seisaku-sho)

In the following compounds, Me represents a methyl group, and Et represents an ethyl group.

Example 1

Synthesis of (1R, 6S)-2,2,6-trimethyl-N-phenethyl-cyclohexane-1-carboxamide (Exemplary compound (1R, 6S)-10-1)

[Chem. 22]

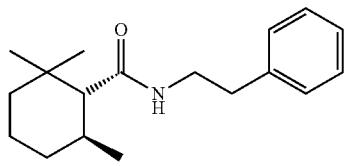

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.4 eq.), and acetonitrile (10 mL) were added to a 50 mL two neck flask under a nitrogen atmosphere. Methanesulfonyl chloride (0.55 mL, 1.2 eq.) was slowly dropped therein at room temperature, followed by performing stirring for 20 minutes at room temperature, and then phenethylamine (0.81 mL, 1.1 eq.) was added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with heptane/ethyl acetate, thereby obtaining a target compound (1.08 g, yield 68%) as a white solid.

Melting Point: 79° C. to 82° C.

HRMS: Mass 273.2093 Actual Measurement Value: 273.2080 ([M]$^+$)

$^1$H-NMR (500 MHz, CDCl$_3$): δ 0.84 (d, 3H, J=6.4 Hz), 0.85-0.92 (m, 1H), 0.93 (s, 3H), 1.04 (s, 3H), 1.11 (dt, 1H, J=4.8, 12.9 Hz), 1.36-1.42 (m, 2H), 1.45-1.59 (m, 2H), 1.70-1.78 (m, 1H), 1.84-1.95 (m, 1H), 3.80 (s, 3H), 4.34 (dd, 1H, J=5.2, 14.3 Hz), 4.44 (dd, 1H, J=4.8, 14.4, Hz), 5.55 (br, 1H), 6.84-6.88 (m, 2H), 7.19-7.23 (m, 2H).

Example 2

Synthesis of (1R, 6S)-N-(2-hydroxy-2-phenylethyl)-2,2,6-trimethylcyclohexane-1-carboxamide (Exemplary Compound (1R, 6S)-10-4)

[Chem. 23]

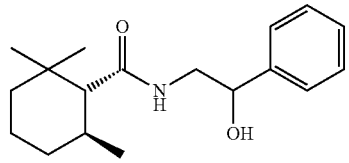

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 20 minutes at room temperature, and then 2-amino-1-phenylethanol (0.97 g, 1.20 eq.) was added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, isolation and purification were performed by silica gel column chromatography (hexane/ethyl acetate=2/1), thereby obtaining a target compound (1.32 g, yield 78%) as a pale yellow crystal.

Melting Point: 95° C. to 98° C.

HRMS: Mass 290.2115 Actual Measurement Value 290.2115 ([M+H]$^+$)

$^1$H-NMR (500 MHz, CDCl$_3$): δ 0.78-0.94 (m, 7H), 0.96-1.04 (m, 3H), 1.06-1.16 (m, 1H), 1.35-1.55 (m, 4H), 1.69-1.76 (m, 1H), 1.81-1.91 (m, 1H), 3.32-3.46 (m, 1H), 3.66-3.81 (m, 2H), 4.82-4.89 (m, 1H), 5.81-5.91 (br, 1H), 7.25-7.29 (m, 1H), 7.31-7.39 (m, 4H).

Example 3

Synthesis of (1S, 6R)-N-(2-hydroxy-2-phenylethyl)-2,2,6-trimethylcyclohexane-1-carboxamide (Exemplary Compound (1S, 6R)-10-4)

[Chem. 24]

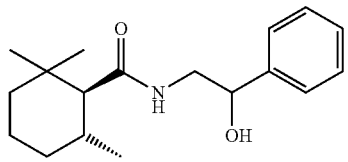

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 20 minutes at room temperature, and then 2-amino-1-phenylethanol (0.97 g, 1.20 eq.) was added thereto and was allowed to react with them for 30 minutes at room temperature. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ethyl acetate=3/1), thereby obtaining a target compound (1.36 g, yield 80%) as a light yellow amorphous solid.

Melting Point: 96° C. to 99° C.

HRMS: Mass 290.2115 Actual Measurement Value 290.2115 ([M+H]$^+$)

$^1$H-NMR (500 MHz, CDCl$_3$): δ 0.78-0.95 (m, 7H), 0.95-1.04 (m, 3H), 1.06-1.17 (m, 1H), 1.36-1.55 (m, 4H), 1.67-1.78 (m, 1H), 1.79-1.91 (m, 1H), 3.32-3.46 (m, 1H), 3.63-3.77 (m, 2H), 3.86-3.95 (m, 1H), 4.82-4.89 (m, 1H), 5.89-5.97 (m, 1H), 7.25-7.29 (m, 1H), 7.31-7.39 (m, 4H).

Example 4

Synthesis of (1R, 6S)-N-((R)-2-hydroxy-2-phenylethyl)-2,2,6-trimethylcyclohexane-1-carboxamide (Exemplary Compound (1R, 6S)-10-5)

[Chem. 25]

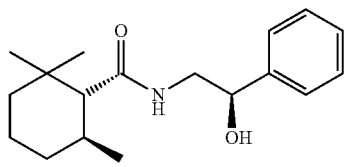

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 25 minutes at room temperature, and then (R)-2-amino-1-phenylethanol (0.97 g, 1.20 eq.) was added thereto and allowed to react with them at room temperature for one hour. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (20 mL), and further washed once with a saturated saline solution (15 mL), followed by drying with sodium sulfate. The obtained solution was concentrated under reduced pressure, and isolation and purification were performed by silica gel column chromatography (hexane/ethyl acetate=2/1), thereby obtaining a target compound (1.37 g, yield 81%) as a light yellow amorphous solid.

HRMS: Mass 290.2115 Actual Measurement Value 290.2113 ([M+H]$^+$)

$^1$H-NMR (500 MHz, CDCl$_3$): δ 0.84 (d, 3H, J=6.3 Hz), 0.83-0.91 (m, 1H), 0.91 (s, 3H), 1.00 (s, 3H), 1.07-1.15 (m, 1H), 1.35-1.54 (m, 4H), 1.68-1.77 (m, 1H), 1.82-1.91 (m, 1H), 3.31-3.39 (m, 1H), 3.74-3.79 (m, 2H), 4.82-4.88 (m, 1H), 5.84 (br, 1H), 7.24-7.29 (m, 1H), 7.31-7.39 (m, 4H).

Example 5

Synthesis of (1S, 6R)-N-((R)-2-hydroxy-2-phenylethyl)-2,2,6-trimethylcyclohexane-1-carboxamide (Exemplary Compound (1S, 6R)-10-5)

[Chem. 26]

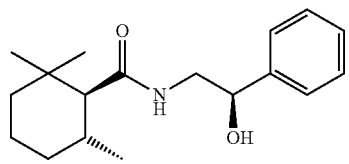

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 20 minutes at room temperature, and then (R)-2-amino-1-phenylethanol (0.97 g, 1.20 eq.) was added thereto and was allowed to react with them for one hour at room temperature. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (20 mL), and further washed once with a saturated saline solution (15 mL), followed by drying with sodium sulfate. The obtained solution was concentrated under reduced pressure, and isolation and purification were performed by silica gel column chromatography (hexane/ethyl acetate=2/1), thereby obtaining a target compound (1.17 g, yield 69%) as a pale yellow crystal.

Melting Point: 105° C. to 110° C.

HRMS: Mass 290.2115 Actual Measurement Value 290.2115 ([M+H]$^+$)

$^1$H-NMR (500 MHz, CDCl$_3$): δ 0.88 (d, 3H, J=6.3 Hz), 0.80-0.87 (m, 1H), 0.89 (s, 3H), 1.00 (s, 3H), 1.06-1.14 (m, 1H), 1.34-1.43 (m, 1H), 1.44-1.52 (m, 1H), 1.67-1.87 (m, 2H), 3.41 (ddd, 1H, J=5.3, 7.6, 14.1 Hz), 3.65 (ddd, 1H, J=3.3, 6.6, 14.1 Hz), 3.90-3.97 (m, 1H), 4.04 (d, 1H, J=3.6 Hz), 4.79-4.86 (m, 1H), 6.08 (br, 1H), 7.24-7.28 (m, 1H), 7.30-7.38 (m, 4H).

Example 6

Synthesis of (1R, 6S)-N-((S)-2-hydroxy-2-phenylethyl)-2,2,6-trimethylcyclohexane-1-carboxamide (Exemplary Compound (1R, 6S)-10-6)

[Chem. 27]

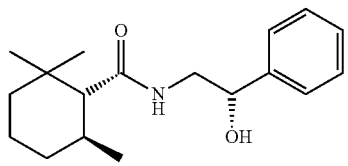

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 20 minutes at room temperature, and then (S)-2-amino-1-phenylethanol (1.00 g, 1.23 eq.) was added thereto and was allowed to react with them at room temperature for one hour. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ethyl acetate=2/1), thereby obtaining a target compound (1.27 g, yield 74%) as a pale yellow crystal.

Melting Point: 107° C. to 111° C.

HRMS: Mass 290.2115 Actual Measurement Value 290.2113 ([M+H]$^+$)

$^1$H-NMR (500 MHz, CDCl$_3$): δ 0.78 (d, 3H, J=6.3 Hz), 0.81-0.87 (m, 1H), 0.89 (s, 3H), 1.00 (s, 3H), 1.06-1.14 (m, 1H), 1.32-1.55 (m, 4H), 1.68-1.90 (m, 2H), 3.42 (ddd, 1H, J=5.3, 7.4, 14.1 Hz), 3.66 (ddd, 1H, J=3.3, 6.6, 14.1 Hz), 3.90-3.97 (m, 1H), 4.82-4.86 (m, 1H), 5.97 (br, 1H), 7.24-7.29 (m, 1H), 7.31-7.39 (m, 4H).

Example 7

Synthesis of (1S, 6R)-N-((S)-2-hydroxy-2-phenylethyl)-2,2,6-trimethylcyclohexane-1-carboxamide (Exemplary Compound (1S, 6R)-10-6)

[Chem. 28]

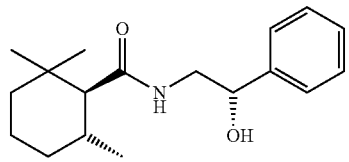

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 20 minutes at room temperature, and then (S)-2-amino-1-phenylethanol (1.00 g, 1.20 eq.) was added thereto and was allowed to react with them for one hour at room temperature. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ethyl acetate=2/1), thereby obtaining a target compound (1.27 g, yield 72%) as a light yellow amorphous solid.

HRMS: Mass 290.2115 Actual Measurement Value 290.2113 ([M+H]$^+$)

$^1$H-NMR (500 MHz, CDCl$_3$): δ 0.84 (d, 3H, J=6.3 Hz), 0.85-0.91 (m, 1H), 0.91 (s, 3H), 0.99 (s, 3H), 1.11 (dt, 1H, J=5.9, 12.8 Hz), 1.36-1.54 (m, 4H), 1.70-1.77 (m, 1H), 1.82-1.91 (m, 1H), 3.36 (dq, 1H, J=2.0, 5.3 Hz), 3.72-3.79 (m, 2H), 4.84-4.89 (n, 1H), 5.86 (br, 1H), 7.24-7.29 (m, 1H), 7.32-7.39 (m, 4H).

Example 8

Synthesis of (1R, 6S)-N-(4-hydroxyphenethyl)-2,2,6-trimethylcyclohexane-1-carboxamide (Exemplary Compound (1R, 6S)-10-8)

[Chem. 29]

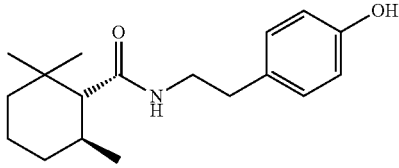

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 30 minutes at room temperature, and then tyramine (0.97 g, 1.20 eq.) was added thereto and allowed to react with them at room temperature for one hour. The reaction solution was diluted with ethyl acetate (10 mL) and n-butanol (10 mL), and then 2N hydrochloric acid (30 mL) was slowly added thereto as a post-treatment. The oil layer was washed twice with a saturated aqueous solution of sodium bicarbonate (20 mL), and further washed once with a saturated saline solution (15 mL), followed by drying with sodium sulfate. The obtained solution was concentrated under reduced pressure, and recrystallized with ethyl acetate/methanol, thereby obtaining a target compound (0.45 g, yield 27%) as a white crystal.

Melting Point: 178° C. to 180° C.

HRMS: Mass 290.2115 Actual Measurement Value 290.2114 ([M+H]$^+$)

$^1$H-NMR (500 MHz, DMSO-d$_6$): δ 0.69 (d, 3H, J=6.3 Hz), 0.75-0.87 (m, 4H), 0.90 (s, 3H), 1.02-1.11 (m, 1H), 1.26-1.32 (m, 1H), 1.40-1.47 (m, 2H), 1.50 (d, 1H, J=11.1 Hz), 1.61-1.76 (m, 2H), 2.58 (t, 2H, J=6.7 Hz), 3.22 (dt, 1H, J=6.7, 7.9 Hz), 6.63-6.68 (m, 2H), 6.99 (d, 2H, J=8.5 Hz), 7.72 (br, 1H), 9.12 (s, 1H).

Example 9

Synthesis of (1S, 6R)-N-(4-hydroxyphenethyl)-2,2,6-trimethylcyclohexane-1-carboxamide (Exemplary Compound (1S, 6R)-10-8)

[Chem. 30]

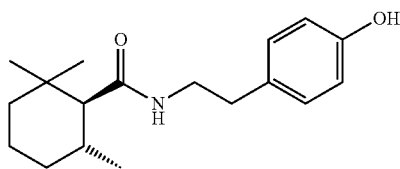

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 20 minutes at room temperature, and then tyramine (0.97 g, 1.20 eq.) was added thereto and was allowed to react with them for one hour at room temperature. The reaction solution was diluted with ethyl acetate (10 mL) and n-butanol (10 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (15 mL), followed by drying with sodium sulfate. The obtained solution was concentrated under reduced pressure, and recrystallized with ethyl acetate/methanol, thereby obtaining a target compound (0.84 g, yield 49%) as a white crystal.

Melting Point: 180° C. to 182° C.

HRMS: Mass 290.2115 Actual Measurement Value 290.2113 ([M +H]$^+$)

$^1$H-NMR (500 MHz, DMSO-d6): δ 0.69 (d, 3H, J=6.3 Hz), 0.75-0.87 (m, 4H), 0.90 (s, 3H), 1.02-1.11 (m, 1H), 1.26-1.32 (m, 1H), 1.40-1.47 (m, 2H), 1.50 (d, 1H, J=11.1 Hz), 1.61-1.76 (m, 2H), 2.58 (t, 2H, J=6.7 Hz), 3.22 (dt, 1H, J=6.7, 7.9 Hz), 6.63-6.68 (m, 2H), 6.99 (d, 2H, J=8.5 Hz), 7.72 (br, 1H), 9.12 (s, 1H).

Example 10

Synthesis of (1R, 6S)-2,2,6-trimethyl-N-(2-oxo-2-phenylethyl) cyclohexane-1-carboxamide (Exemplary Compound (1R)-10-10) and (1S, 6S)-2,2,6-trimethyl-N-(2-oxo-2-phenylethyl) cyclohexane-1-carboxamide (Exemplary Compound (1S)-10-10)

[Chem. 31]

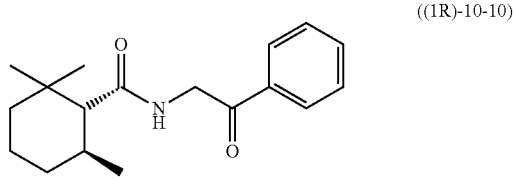

[Chem. 32]

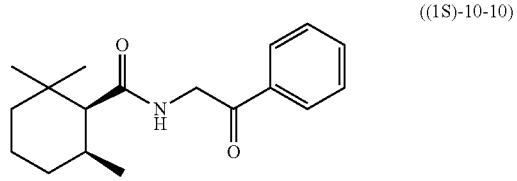

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.4 eq.), and acetonitrile (10 mL) were added to a 50 mL two neck flask under a nitrogen atmosphere. Methanesulfonyl chloride (0.55 mL, 1.2 eq.) was slowly dropped therein at room temperature, followed by performing stirring for 5 hours at room temperature, and then phenacylamine hydrochloride (1.11 g, 1.1 eq.) and triethylamine (0.98 mL, 1.2 eq.) were added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by column chromatography (hexane/ethyl acetate=2/1), thereby obtaining the exemplary compound (1R)-10-10 (0.81 g, yield 58%) as a white solid and obtaining the exemplary compound (1S)-10-10 (0.22 g, yield 13%) as an amorphous solid.

Exemplary Compound (1R)-10-10
Melting Point: 85° C. to 87° C.
HRMS: Mass 288.1958 Actual Measurement Value 288.1972 ([M+H]$^+$)
$^1$-NMR (500 MHz, CDCl$_3$): δ 0.86 (d, 3H, J=6.4 Hz), 0.86-0.98 (m, 1H), 0.98 (s, 3H), 1.04 (s, 3H), 1.19 (dt, 1H, J=12.8, 5.0 Hz), 1.39-1.45 (m, 2H), 1.49-1.58 (m, 2H), 1.63 (d, 1H, J=11.1 Hz), 1.73-1.79 (m, 1H), 1.84-1.97 (m, 1H), 4.80 (d, 2H, J=4.3 Hz), 6.47 (br, 1H), 7.48-7.53 (m, 2H), 7.60-7.65 (m, 1H), 7.96-8.02 (m, 2H).

Exemplary Compound (1S)-10-10
HRMS: Mass 288.1958 Actual Measurement Value 288.1945 ([M +H]$^+$)
$^1$H-NMR (500 MHz, CDCl$_3$): δ 0.89 (d, 3H, J=6.3 Hz), 0.93 (s, 3H), 1.02 (s, 3H), 1.09-1.14 (m, 1H), 1.34-1.52 (m, 2H), 1.59-2.00 (m, 5H), 4.75 (d, 2H, J=4.0 Hz), 6.48 (br, 1H), 7.48-7.53 (m, 2H), 7.58-7.65 (m, 1H), 7.96-8.01 (m, 2H).

Example 11

Synthesis of (1S, 6R)-2,2,6-trimethyl-N-(2-oxo-2-phenylethyl) cyclohexane-1-carboxamide (Exemplary Compound (1S)-10-11) and (1R, 6R)-2,2,6-trimethyl-N-(2-oxo-2-phenylethyl) cyclohexane-1-carboxamide (Exemplary compound (1R)-10-11)

[Chem. 33]

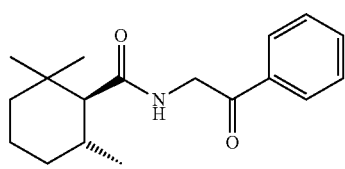

((1S)-10-11)

[Chem. 34]

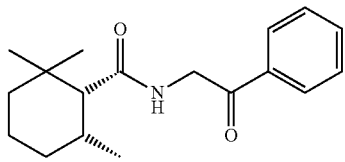

((1R)-10-11)

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.4 eq.), and acetonitrile (10 mL) were added to a 50 mL two neck flask under a nitrogen atmosphere. Methanesulfonyl chloride (0.55 mL, 1.2 eq.) was slowly dropped therein at room temperature, followed by performing stirring for 5 hours at room temperature, and then phenacylamine hydrochloride (1.11 g, 1.1 eq.) and triethylamine (0.98 mL, 1.2 eq.) were added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by column chromatography (hexane/ethyl acetate=2/1), thereby obtaining the exemplary compound (1S)-10-11 (0.58 g, yield 34%) as a white solid and obtaining the exemplary compound (1R)-10-11 (0.29 g, yield 17%) as an amorphous solid.

Exemplary Compound (1S)-10-11
Melting Point: 86° C. to 87° C.
HRMS: Mass 288.1958 Actual Measurement Value 288.1934 ([M+H]$^+$)
$^1$H-NMR (500 MHz, CDCl$_3$): δ 0.86 (d, 3H, J=6.4 Hz), 0.86-0.98 (m, 1H), 0.98 (s, 3H), 1.04 (s, 3H), 1.19 (dt, 1H, J=12.8, 5.0 Hz), 1.37-1.45 (m, 2H), 1.49-1.58 (m, 2H), 1.63 (d, 1H, J=11.1 Hz), 1.73-1.79 (m, 1H), 1.85-1.97 (m, 1H), 4.80 (d, 2H, J=4.3 Hz), 6.47 (br, 1H), 7.48-7.53 (m, 2H), 7.60-7.65 (m, 1H), 7.96-8.01 (m, 2H).

Exemplary Compound (1R)-10-11
HRMS: Mass 288.1958 Actual Measurement Value 288.1990 ([M+H]$^+$)
$^1$H-NMR (500 MHz, CDCl$_3$): δ 0.89 (d, 3H, J=6.3 Hz), 0.93 (s, 3H), 1.02 (s, 3H), 1.09-1.14 (m, 1H), 1.34-1.52 (m, 2H), 1.59-1.98 (m, 5H), 4.75 (d, 2H, J=4.0 Hz), 6.48 (br, 1H), 7.46-7.53 (m, 2H), 7.58-7.65 (m, 1H), 7.94-8.02 (m, 2H).

Example 12

Synthesis of (1R, 6S)-N-(4-methoxyphenethyl)-2,2,6-trimethylcyclohexane-1-carboxamide (Exemplary Compound (1R, 6S)-10-12)

[Chem. 35]

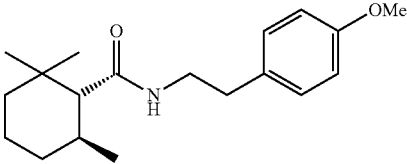

(1R, 6S)-2,2,6-trimethylcyclohexanecarboxylic acid ((1R, 6S)-5) (1.00 g, 5.87 mmol) which was obtained according to the method described in PTL 29, thionyl chloride (0.47 mL, 1.10 eq.), toluene (10 mL) and a few drops of dimethyl formamide (DMF) were added to a 100 mL four neck flask under a nitrogen atmosphere, and they were stirred for one hour at room temperature. A solution which was prepared by adding toluene (5 mL) to 4-(methoxyphenyl) ethylamine (0.95 mL, 1.10 eq.) and triethylamine (1 mL) was slowly added to the inside of the system. After the mixture was stirred for two and a half hours at 60° C., the reaction solution was transferred to a separatory funnel, and dilute hydrochloric acid and ethyl acetate were added thereto to perform washing. The oil layer was washed once with dilute hydrochloric acid, then washed once with a saturated saline solution, followed by drying with anhydrous magnesium sulfate. The obtained solution was concentrated under reduced pressure, and recrystallized with heptane/ethyl acetate, thereby obtaining a target compound (0.87 g, yield 50%) as a white solid.

Melting Point: 75° C. to 77° C.
HRMS: Mass 304.2271 Actual Measurement Value 304.2299 ([M +H]$^+$)
$^1$H-NMR (500 MHz, CDCl$_3$): δ 0.80 (d, 3H, J=6.4 Hz), 0.81-0.87 (m, 1H), 0.88 (s, 3H), 1.00 (s, 3H), 1.09 (dt, 1H, J=12.7, 5.0 Hz), 1.29 (d, 1H, J=11.1 Hz), 1.34-1.38 (m, 1H), 1.42-1.54 (m, 2H), 1.68-1.90 (m, 2H), 2.75 (t, 2H, J=6.9 Hz), 3.45-3.60 (m, 2H), 3.79 (br, 3H), 6.80-6.86 (m, 2H), 7.10-7.14 (m, 2H).

Example 13

Synthesis of (1R, 6S)-N-(2-methoxyphenethyl)-2,2,6-trimethylcyclohexane-1-carboxamide (Exemplary Compound (1R, 6S)-10-13)

[Chem. 36]

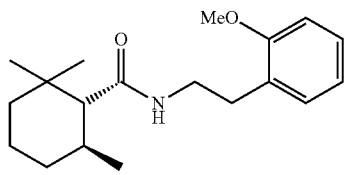

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then 2-(2-methoxyphenyl) ethylamine (1.03 mL, 1.20 eq.) was added thereto and was allowed to react with them for one hour at room temperature. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (1.33 g, yield 75%) as a pale yellow crystal.

Melting Point: 98° C. to 102° C.

HRMS: Mass 304.2271 Actual Measurement Value 304.2276 ([M+H]$^+$)

$^1$H-NMR (500 MHz, CDCl$_3$): δ 0.77 (d, 3H, J=6.4 Hz), 0.81-0.85 (m, 1H), 0.85 (s, 3H), 0.98 (s, 3H), 1.08 (dt, 1H, J=5.2, 12.9 Hz), 1.29 (d, 1H, J=11.1 Hz), 1.32-1.39 (m, 1H), 1.44-1.53 (m, 2H), 1.64-1.75 (m, 1H), 1.78-1.87 (m, 1H), 2.83 (t, 2H, J=6.8 Hz), 3.45-3.58 (m, 2H), 3.84 (s, 3H), 5.55 (br, 1H), 6.85-7.02 (m, 2H), 7.15 (dd, 1H, J=1.4, 7.5 Hz), 7.21 (dt, 1H, J=1.8, 7.8 Hz).

Example 14

Synthesis of (1R, 6S)-N-(3,4-dihydroxyphenethyl)-2,2,6-trimethylcyclohexane-1-carboxamide (Exemplary Compound (1R, 6S)-10-14)

[Chem. 37]

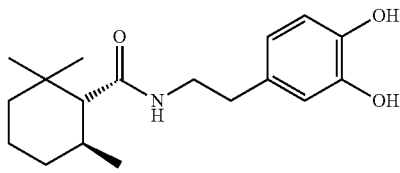

(1R, 6S)-2,2,6-trimethylcyclohexanecarboxylic acid ((1R, 6S)-5) (1.00 g, 5.87 mmol) which was obtained according to the method described in PTL 29, triethylamine (6.53 mL, 4.0 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then dopamine hydrochloride (1.23 g, 1.10 eq.) was added thereto and was allowed to react with them for one hour at 50° C. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by column chromatography (ethyl acetate/methanol=10/0 to 10/1), thereby obtaining a target compound (1.28 g, yield 71%) as an amorphous solid.

HRMS: Mass 306.2061 Actual Measurement Value 306.2064 ([M+H]$^+$)

$^1$H-NMR (500 MHz, DMSO-d$_6$): δ 0.70 (d, 3H, J=6.3 Hz), 0.76-0.85 (m, 5H), 0.86-0.93 (m, 4H)), 1.01-1.11 (m, 1H), 1.26-1.33 (m, 1H), 1.39-1.47 (m, 2H), 1.50 (d, 1H, J=11.0 Hz), 1.61-1.75 (m, 2H), 3.14-3.22 (m, 2H), 6.43 (dd, 1H, J=8.0, 2.0 Hz), 6.57 (d, 1H, J=1.9 Hz), 6.61 (d, 1H, J=7.9 Hz), 7.71 (br, 1H), 8.60 (s, 1H), 8.68 (s, 1H).

Example 15

Synthesis of (1R, 6S)-N-(3,4-dimethoxyphenethyl)-2,2,6-trimethylcyclohexane-1-carboxamide (Exemplary Compound (1R, 6S)-10-15)

[Chem. 38]

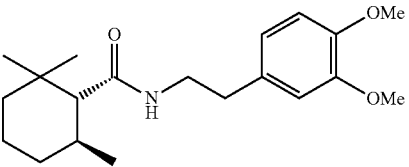

(1R, 6S)-2,2,6-trimethylcyclohexanecarboxylic acid ((1R, 6S)-5) (1.00 g, 5.87 mmol) which was obtained according to the method described in PTL 29, thionyl chloride (0.47 mL, 1.10 eq.), toluene (10 mL) and a few drops of dimethyl formamide (DMF) were added to a 100 mL four neck flask under a nitrogen atmosphere, and they were stirred for one hour at room temperature. A solution which was prepared by adding toluene (5 mL) to homoveratrylamine (1.35 mL, 1.10 eq.) and triethylamine (1 mL) was slowly added to the inside of the system. After two and a half hours, the reaction solution was transferred to a separatory funnel, and dilute hydrochloric acid and ethyl acetate were added thereto to perform washing. The oil layer was washed once with dilute hydrochloric acid, then washed once with a saturated saline solution, followed by drying with anhydrous magnesium sulfate. The obtained solution was concentrated under reduced pressure, and recrystallized with heptane/ethyl acetate, thereby obtaining a target compound (1.55 g, yield 79%) as a white crystal.

Melting Point: 93° C. to 96° C.

HRMS: Mass 356.2196 Actual Measurement Value 356.2203 ([M+Na]$^+$)

$^1$H-NMR (500 MHz, CDCl$_3$): δ 0.80 (d, 3H, J=6.4 Hz), 0.81-0.87 (m, 1H), 0.88 (s, 3H), 1.00 (s, 3H), 1.09 (dt, 1H, J=12.7, 5.0 Hz), 1.31 (d, 1H, J=11.1 Hz), 1.34-1.38 (m, 1H), 1.42-1.54 (m, 2H), 1.68-1.90 (m, 2H), 2.76 (t, 2H, J=7.0 Hz), 3.55-3.60 (m, 2H), 3.86 (br, 6H), 6.70-6.83 (m, 3H).

Example 16

Synthesis of (1R, 6S)-N-(2-(1H-indol-3-yl) ethyl)-2,2,6-trimethylcyclohexane-1-carboxamide (Exemplary compound (1R, 6S)-10-19)

[Chem. 39]

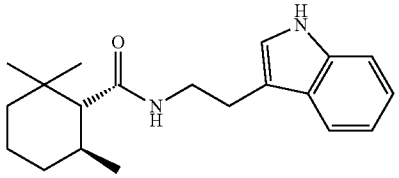

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then tryptamine (0.97 g, 1.20 eq.) was added thereto and was allowed to react with them for one hour at room temperature. The reaction solution was diluted with ethyl acetate (15 mL), and then water (10 mL) and a saturated aqueous solution of ammonium chloride (10 mL) were slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ethyl acetate=2/1), thereby obtaining a target compound (0.96 g, yield 52%) as a white crystal.

Melting Point: 132° C. to 135° C.

HRMS: Mass 313.2274 Actual Measurement Value 313.2276 ([M+H]$^+$)

$^1$H-NMR (500 MHz, CDCl$_3$): δ 0.80 (d, 3H, J=6.4 Hz), 0.80-0.86 (m, 1H), 0.87 (s, 3H), 1.00 (s, 3H), 1.07 (dt, 1H, J=5.0, 12.9 Hz), 1.29 (d, 1H, J=11.1 Hz), 1.32-1.38 (m, 1H), 1.43-1.54 (m, 2H), 1.67-1.74 (m, 1H), 1.78-1.90 (m, 1H), 2.98 (t, 2H, J=6.8 Hz), 3.67-3.71 (m, 2H), 5.58 (br, 1H), 7.02 (d, 1H, J=2.3 Hz), 7.12 (dt, 1H, J=1.0, 7.0 Hz), 7.20 (dt, 1H, J=1.0, 7.1 Hz), 7.37 (dt, 1H, J=0.9, 8.0 Hz), 7.61 (dd, 1H, J=0.5, 8.0 Hz), 8.27 (br, 1H).

Example 17

Synthesis of (1R, 6S)-2,2,6-trimethyl-N-(2-pyridinylmethyl) cyclohexane-1-carboxamide (Exemplary Compound (1R, 6S)-10-22)

[Chem. 40]

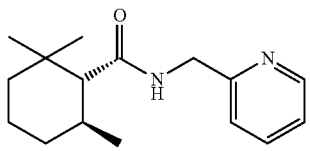

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. After they were stirred for 20 minutes at room temperature, 2-(2-aminomethyl) pyridine (0.72 mL, 1.20 eq.) was slowly added thereto and allowed to react at room temperature for one hour. The reaction solution was diluted with ethyl acetate (10 mL), and then water (10 mL) and a saturated aqueous ammonium chloride solution (15 mL) were slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (0.89 g, yield 58%) as a white crystal.

Melting Point: 95° C. to 96° C.

HRMS: Mass 261.1961 Actual Measurement Value 261.1962 ([M+H]$^+$)

$^1$H-NMR (500 MHz, CDCl$_3$): δ 0.82 (d, 3H, J=6.4 Hz), 0.84-0.92 (m, 1H), 0.88 (s, 3H), 1.04 (s, 3H), 1.16 (dt, 1H, J=5.0, 13.0 Hz), 1.36-1.43 (m, 1H), 1.45-1.54 (m, 2H), 1.56 (d, 1H, J=11.2 Hz), 1.71-1.77 (m, 1H), 1.85-1.95 (m, 1H), 4.54 (dd, 1H, J=5.0, 16.1 Hz), 4.60 (dd, 1H, J=5.2, 16.1 Hz), 6.66 (br, 1H), 7.17-7.21 (m, 1H), 7.29 (d, 1H, J=7.8 Hz), 7.65 (dt, 1H, J=1.8, 7.8 Hz), 8.51-8.54 (m, 1H).

Example 18

Synthesis of (1R, 6S)-2,2,6-trimethyl-N-(2-pyridinylethyl) cyclohexane-1-carboxamide (Exemplary Compound (1R, 6S)-10-23)

[Chem. 41]

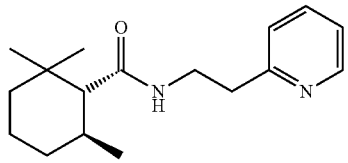

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. After they were stirred for 20 minutes at room temperature, 2-(2-aminoethyl) pyridine (0.84 mL, 1.20 eq.) was slowly added thereto and allowed to react with them at room temperature for 30 minutes. The reaction solution was diluted with ethyl acetate (10 mL), and then a saturated aqueous solution of ammonium chloride (20 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (1.04 g, yield 64%) as a yellow crystal.

Melting Point: 91° C. to 96° C.

HRMS: Mass 275.2118 Actual Measurement Value 275.2118 ([M+H]$^+$)

$^1$H-NMR (500 MHz, CDCl$_3$): δ 0.86 (d, 3H, J=6.4 Hz), 0.78-0.89 (m, 1H), 0.84 (s, 3H), 0.98 (s, 3H), 1.10 (dt, 1H, J=5.1, 12.9 Hz), 1.33-1.48 (m, 2H), 1.44-1.53 (m, 2H), 1.67-1.75 (m, 1H), 1.78-1.88 (m, 1H), 3.00 (t, 2H, J=6.4 Hz), 3.63-3.74 (m, 2H), 6.25 (br, 1H), 7.11-7.17 (m, 1H), 7.18 (d, 1H, J=7.8 Hz), 7.60 (dt, 1H, J=1.9, 7.8 Hz), 8.51-8.54 (m, 1H).

Example 19

Synthesis of (1R, 6S)-2,2,6-trimethyl-N-(2-thiophenylmethyl) cyclohexane-1-carboxamide (Exemplary Compound (1R, 6S)-10-26)

[Chem. 42]

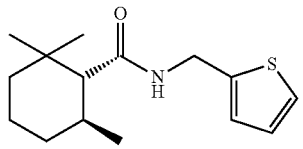

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 25 minutes at room temperature, and then 2-(aminomethyl) thiophene (0.59 mL, 1.20 eq.) was added thereto and allowed to react with them at room temperature for one and a half hours. The reaction solution was diluted with ethyl acetate (10 mL), and then 2N hydrochloric acid (10 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (1.14 g, yield 73%) as a pale yellow solid.

Melting Point: 88° C. to 90° C.

HRMS: Mass 266.1573 Actual Measurement Value 266.1577 ([M +H]$^+$)

$^1$H-NMR (500 MHz, CDCl$_3$): δ 0.84 (d, 3H, J=6.3 Hz), 0.85-0.92 (m, 1H), 0.94 (s, 3H), 1.06 (s, 3H), 1.12 (dt, 1H, J=5.1, 12.9 Hz), 1.36-1.44 (m, 2H), 1.46-1.55 (m, 2H), 1.71-1.78 (m, 1H), 1.84-1.95 (m, 1H), 4.60 (dd, 1H, J=5.5, 15.2 Hz), 4.66 (dd, 1H, J=5.7, 15.2 Hz), 5.55 (br, 1H), 6.92-6.98 (m, 2H), 7.18-7.24 (m, 1H).

Example 20

Synthesis of (1S, 6R)-2,2,6-trimethyl-N-(2-thiophenylmethyl) cyclohexane-1-carboxamide (Exemplary Compound (1S, 6R)-10-26)

[Chem. 43]

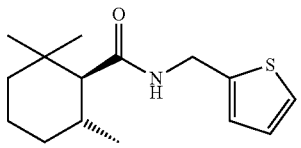

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.4 eq.), and acetonitrile (10 mL) were added to a 50 mL two neck flask under a nitrogen atmosphere. Methanesulfonyl chloride (0.55 mL, 1.2 eq.) was slowly dropped therein at room temperature, followed by performing stirring for 20 minutes at room temperature, and then 2-(2-aminomethyl) thiophene (0.59 mL, 1.2 eq.) was added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with heptane/ethyl acetate, thereby obtaining a target compound (0.95 g, yield 61%) as a white solid.

Melting Point: 88° C. to 90° C.

HRMS: Mass 266.1573 Actual Measurement Value 266.1562 ([M+H]⁺)

¹H-NMR (500 MHz, CDCl₃): δ 0.84 (d, 3H, J=6.4 Hz), 0.85-0.92 (m, 1H), 0.93 (s, 3H), 1.04 (s, 3H), 1.12 (dt, 1H, J=12.8, 5.0 Hz), 1.36-1.42 (m, 2H), 1.45-1.60 (m, 2H), 1.70-1.78 (m, 1H), 1.84-1.95 (m, 1H), 4.56-4.69 (m, 2H), 5.69 (br, 1H), 6.91-6.98 (m, 2H), 7.19-7.23 (m, 1H).

Example 21

Synthesis of (1R, 6S)-2,2,6-trimethyl-N-(3-thiophenylmethyl) cyclohexane-1-carboxamide (Exemplary Compound (1R, 6S)-10-27)

[Chem. 44]

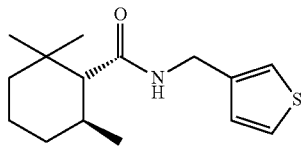

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. After they were stirred for 20 minutes at room temperature, 3-thiophenemethylamine (0.59 mL, 1.20 eq.) was slowly added thereto and allowed to react with them at room temperature for one hour. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (1.12 g, yield 77%) as a pale yellow solid.

Melting Point: 82° C. to 84° C.

HRMS: Mass 266.1573 Actual Measurement Value 266.1571 ([M+H]⁺)

¹H-NMR (500 MHz, CDCl₃): δ 0.84 (d, 3H, J=6.3 Hz), 0.85-0.92 (m, 1H), 0.93 (s, 3H), 1.03 (s, 3H), 1.12 (dt, 1H, J=5.1, 13.0 Hz), 1.35-1.43 (m, 2H), 1.46-1.55 (m, 2H), 1.66-1.77 (m, 1H), 1.84-1.95 (m, 1H), 4.42 (dd, 1H, J=5.6, 14.9 Hz), 4.50 (dd, 1H, J=5.9, 14.9 Hz), 5.67 (br, 1H), 7.03 (d, 1H, J=5.0 Hz), 7.12-7.16 (m, 1H), 7.28 (dd, 1H, J=3.0, 5.0 Hz).

Example 22

Synthesis of (1R, 6S)-2,2,6-trimethyl-N-(2-thiophenylethyl) cyclohexane-1-carboxamide (Exemplary Compound (1R, 6S)-10-28)

[Chem. 45]

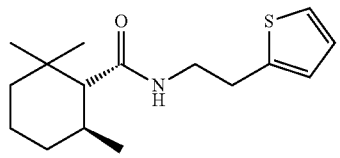

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. Methanesulfonyl chloride (0.55 mL, 1.20 eq.) was slowly dropped therein at room temperature, followed by performing stirring for 15 minutes at room temperature, and then 2-(aminoethyl)thiophene (0.69 mL, 1.20 eq.) was added thereto and allowed to react with them at room temperature for one hour. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane, thereby obtaining a target compound (1.11 g, yield 67%) as a light brown solid.

Melting Point: 83° C. to 86° C.

HRMS: Mass 280.1730 Actual Measurement Value 280.1730 ([M+H]⁺)

¹H-NMR (500 MHz, CDCl₃): δ 0.81 (d, 3H, J=6.3 Hz), 0.81-0.88 (m, 1H), 0.88 (s, 3H), 1.01 (s, 3H), 1.10 (dt, 1H, J=4.8, 12.4 Hz), 1.36 (t, 2H, J=12.4 Hz), 1.44-1.55 (m, 2H), 1.66-1.92 (m, 2H), 3.04 (t, 2H, J=9.7 Hz), 3.47-3.64 (m, 2H), 5.58 (br, 1H), 6.81-6.97 (m, 2H), 7.15 (d, 1H, J=5.0 Hz).

Example 23

Synthesis of (1S, 6R)-2,2,6-trimethyl-N-(2-thiophenylethyl) cyclohexane-1-carboxamide (Exemplary Compound (1S, 6R)-10-28)

[Chem. 46]

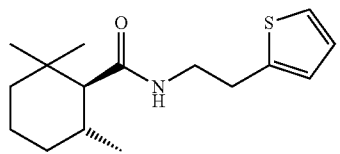

(1S, 6R)-2,2,6-trimethylcyclohexanecarboxylic acid ((1S, 6R)-5) (1.00 g, 5.87 mmol) which was obtained according to the method described in PTL 29, triethylamine (1.95 mL, 2.4 eq.), and acetonitrile (10 mL) were added to a 50 mL two neck flask under a nitrogen atmosphere. Methanesulfonyl chloride (0.55 mL, 1.2 eq.) was slowly dropped therein at room temperature, followed by performing stirring for 20 minutes at room temperature, and then 2-(2-aminoethyl)thiophene (0.71 mL, 1.2 eq.) was added thereto and allowed to react with them at room temperature for 45 minutes. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with heptane/ethyl acetate, thereby obtaining a target compound (0.95 g, yield 61%) as a white solid.

Melting Point: 85° C. to 86° C.

HRMS: Mass 280.1730 Actual Measurement Value 280.1740 ([M+H]$^+$)

$^1$H-NMR (500 MHz, CDCl$_3$): δ 0.81 (d, 3H, J=6.4 Hz), 0.83-0.89 (m, 1H), 0.89 (s, 3H), 1.00 (s, 3H), 1.10 (dt, 1H, J=12.8, 5.0 Hz), 1.32-1.40 (m, 2H), 1.45-1.56 (m, 2H), 1.68-1.75 (m, 1H), 1.81-1.89 (m, 1H), 2.99-3.07 (m, 2H), 3.49-3.64 (m, 2H), 5.48 (br, 1H), 6.84 (dd, 1H, J=3.3, 0.9 Hz), 6.94 (dd, 1H, J=5.1, 3.4 Hz), 7.16 (dd, 1H, J=5.3, 1.1 Hz).

Example 24

Synthesis of (1R, 6S)-N-(4-hydroxyphenyl)-2,2,6-trimethylcyclohexane-1-carboxamide (Exemplary Compound (1R, 6S)-10-33)

[Chem. 47]

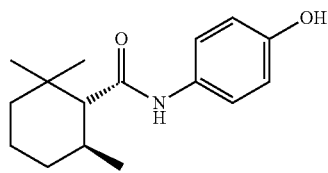

(1R, 6S)-2,2,6-trimethylcyclohexanecarboxylic acid ((1R, 6S)-5) (2.00 g, 11.7 mmol) which was obtained according to the method described in PTL 29, triethylamine (3.80 mL, 2.40 eq.), and acetonitrile (10 mL) were added to a 50 mL two neck flask under a nitrogen atmosphere. The temperature of the inside of the system was lowered to 0° C. to 5° C. by an ice bath and methanesulfonyl chloride (1.10 mL, 1.20 eq.) was dropped therein. The mixture was stirred for 20 minutes at room temperature, and then 4-aminophenol (1.54 g, 1.20 eq.) was added thereto and was allowed to react with them for one hour at room temperature. The reaction solution was diluted with ethyl acetate (15 mL), and then 2N hydrochloric acid (20 mL) was slowly added thereto as a post-treatment. The oil layer was washed twice with a saturated aqueous solution of sodium bicarbonate (20 mL), and further washed once with a saturated saline solution (15 mL), followed by drying with sodium sulfate. The obtained solution was concentrated under reduced pressure, and recrystallized with hexane/ethyl acetate, thereby obtaining a target compound (1.40 g, yield 46%) as a white solid.

Melting Point: 100° C. to 105° C.

HRMS: Mass 262.1802 Actual Measurement Value 262.1804 ([M+H]$^+$)

$^1$H-NMR (500 MHz, DMSO-d$_6$): δ 0.79 (d, 3H, J=6.0 Hz), 0.82-0.92 (m, 1H), 0.92 (s, 3H), 0.96 (s, 3H), 1.10-1.17 (n, 1H), 1.32-1.38 (m, 1H), 1.43-1.52 (m, 2H), 1.67-1.84 (m, 3H), 2.48-2.52 (m, 1H), 6.63-6.68 (m, 2H), 7.31-7.37 (m, 2H), 9.47 (br, 1H).

Example 25

Synthesis of (1R, 6S)-N-(4-methoxyphenyl)-2,2,6-trimethylcyclohexane-1-cathoxamide (Exemplary Compound (1R, 6S)-10-35)

[Chem. 48]

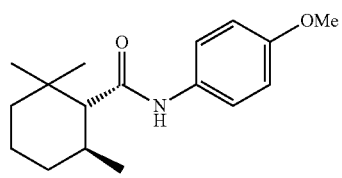

(1R, 6S)-2,2,6-trimethylcyclohexanecarboxylic acid ((1R, 6S)-5) (1.00 g, 5.87 mmol) which was obtained according to the method described in PTL 29, thionyl chloride (0.47 mL, 1.10 eq.), toluene (10 mL) and a few drops of dimethyl formamide (DMF) were added to a 100 mL four neck flask under a nitrogen atmosphere, and they were stirred for one hour at room temperature. A solution which was prepared by adding toluene (5 mL) to p-anisidine (2.17 g, 3.0 eq.) was slowly added to the inside of the system. After five hours at 90° C., the reaction solution was transferred to a separatory funnel, and dilute hydrochloric acid and ethyl acetate were added thereto to perform washing. The oil layer was washed once with dilute hydrochloric acid, then washed once with a saturated saline solution, followed by drying with anhydrous magnesium sulfate. The obtained solution was concentrated under reduced pressure, and recrystallized with heptane/ethyl acetate, thereby obtaining a target compound (1.07 g, yield 66%) as a white crystal.

Melting Point: 143° C. to 144° C.

HRMS: Mass 276.1958 Actual Measurement Value 276.1985 ([M+H]$^+$)

$^1$H-NMR (500 MHz, CDCl$_3$): δ 0.80 (d, 3H, J=6.4 Hz), 0.81-0.87 (m, 1H), 0.88 (s, 3H), 1.00 (s, 3H), 1.18 (dt, 1H, J=12.7, 5.0 Hz), 1.40-1.48 (m, 1H), 1.49-1.60 (m, 3H), 1.76-1.81 (m, 1H), 1.90-2.00 (m, 1H), 3.78 (s, 3H), 6.82-6.87 (m, 2H), 6.95 (br, 6H), 7.37-7.44 (m, 2H).

Example 26

Synthesis of (1R, 6S)-N-(4-methoxybenzyl)-2,2,6-trimethylcyclohexane-1-carboxamide (Exemplary Compound (1R, 6S)-10-36)

[Chem. 49]

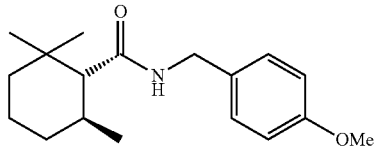

(1R, 6S)-2,2,6-trimethylcyclohexanecarboxylic acid ((1R, 6S)-5) (1.00 g, 5.87 mmol) which was obtained according to the method described in PTL 29, thionyl chloride (0.47 mL, 1.10 eq.), toluene (10 mL) and a few drops of dimethyl formamide (DMF) were added to a 100 mL four neck flask under a nitrogen atmosphere, and they were stirred for one hour at room temperature. A solution which was prepared by adding toluene (5 mL) to 4-methoxybenzylamine (2.28 mL, 3.0 eq.) was slowly added to the inside of the system. After five hours at 90° C., the reaction solution was transferred to a separatory funnel, and dilute hydrochloric acid and ethyl acetate were added thereto to perform washing. The oil layer was washed once with dilute hydrochloric acid, then washed once with a saturated saline solution, followed by drying with anhydrous magnesium sulfate. The obtained solution was concentrated under reduced pressure, and recrystallized with heptane/ethyl acetate, thereby obtaining a target compound (1.13 g, yield 66%) as a white crystal.

Melting Point: 85° C. to 87° C.

HRMS: Mass 289.2042 Actual Measurement Value 289.2031 ([M]$^+$)

$^1$H-NMR (500 MHz, CDCl$_3$): δ 0.84 (d, 3H, J=6.4 Hz), 0.85-0.92 (m, 1H), 0.93 (s, 3H), 1.04 (s, 3H), 1.11 (dt, 1H, J=12.9, 4.8 Hz), 1.36-1.42 (m, 2H), 1.45-1.59 (m, 2H), 1.70-1.78 (m, 1H), 1.84-1.95 (m, 1H), 3.80 (s, 3H), 4.34 (dd, 1H, J=14.3, 5.2 Hz), 4.44 (dd, 1H, J=14.4, 4.8 Hz), 5.55 (br, 1H), 6.84-6.88 (m, 2H), 7.19-7.23 (m, 2H).

Example 27

Synthesis of (1R, 6S)-N-(benzo[d][1,3]dioxol-5-yl)-2,2,6-trimethylcyclohexane-1-carboxamide (Exemplary Compound (1R, 6S)-10-38)

[Chem. 50]

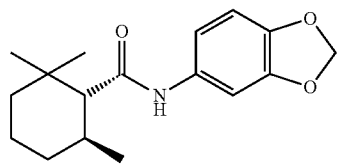

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then 3,4-methylenedioxyaniline (0.97 g, 1.20 eq.) was added thereto and was allowed to react with them for one hour at 50° C. in an oil bath. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane/ethyl acetate, thereby obtaining a target compound (0.63 g, yield 37%) as a gray solid.

Melting Point: 171° C. to 173° C.

HRMS: Mass 290.1751 Actual Measurement Value 290.1754 ([M+H]$^+$)

$^1$H-NMR (500 MHz, CDCl$_3$): δ 0.91 (d, 3H, J=6.4 Hz), 0.91-1.00 (m, 1H), 1.02 (s, 3H), 1.07 (s, 3H), 1.18 (dt, 1H, J=5.5, 12.8 Hz), 1.40-1.47 (m, 1H), 1.49-1.58 (m, 2H), 1.74-1.82 (m, 1H), 1.91-2.00 (m, 1H), 5.93 (s, 2H), 6.72 (d, 1H, J=8.3 Hz), 6.77 (dd, 1H, J=2.1, 8.3 Hz), 7.02 (br, 1H), 7.24 (d, 1H, J=2.1 Hz).

Example 28

Synthesis of (1R, 6S)-N-(4-acetylphenyl)-2,2,6-trimethylcyclohexane-1-carboxamide (Exemplary Compound (1R, 6S)-10-41)

[Chem. 51]

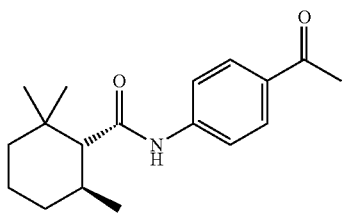

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then 4'-aminoacetophenone (0.97 g, 1.20 eq.) was added thereto and was allowed to react with them for two hours at 50° C. in an oil bath. The reaction solution was diluted with ethyl acetate (15 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ethyl acetate), thereby obtaining a target compound (0.45 g, yield 27%) as a pale yellow solid.

Melting Point: 166° C. to 168° C.

HRMS: Mass 288.1958 Actual Measurement Value 288.1952 ([M+H]$^+$)

$^1$H-NMR (500 MHz, CDCl$_3$): δ 0.91 (d, 3H, J=6.4 Hz), 0.93-1.00 (m, 1H), 1.04 (s, 3H), 1.08 (s, 3H), 1.19 (dt, 1H, J=5.9, 13.0 Hz), 1.40-1.56 (m, 3H), 1.61 (d, 1H, J=11.2 Hz), 1.75-1.83 (m, 1H), 1.93-2.05 (m, 1H), 2.57 (s, 3H), 7.43 (br, 1H), 7.62-7.67 (m, 2H), 7.91-7.95 (m, 2H).

Example 29

Synthesis of (1R, 6S)-N-(4-(2-hydroxyethyl) phenyl)-2,2,6-trimethylcyclohexane-1-carboxamide (Exemplary Compound (1R, 6S)-10-42)

[Chem. 52]

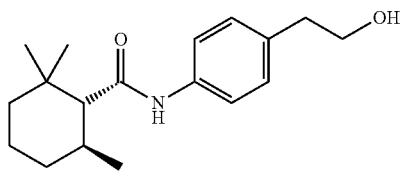

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then 2-(4-aminophenyl) ethanol (0.97 g, 1.20 eq.) was added thereto and was allowed to react with them for one hour at 60° C. in an oil bath. The reaction solution was diluted with ethyl acetate (10 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ ethyl acetate), thereby obtaining a target compound (0.73 g, yield 43%) as a pale yellow solid.

Melting Point: 98° C. to 103° C.

HRMS: Mass 290.2115 Actual Measurement Value 290.2111 ([M+H]$^+$)

$^1$H-NMR (500 MHz, CDCl$_3$): δ 0.91 (d, 3H, J=6.4 Hz), 0.93-1.00 (m, 1H), 1.03 (s, 3H), 1.07 (s, 3H), 1.19 (dt, 1H, J=5.4, 13.1 Hz), 1.42-1.47 (m, 1H), 1.49-1.56 (m, 2H), 1.58 (d, 1H, J=11.0 Hz), 1.67 (br, 1H), 1.75-1.83 (m, 1H), 1.91-2.02 (m, 1H), 2.80-2.84 (m, 2H), 3.78-3.86 (m, 2H), 7.14-7.23 (m, 3H), 7.42-7.47 (m, 2H).

Example 30

Synthesis of methyl 4-((1R, 6S)-2,2,6-trimethylcyclohexane-1-carboxamide) benzoate (Exemplary Compound (1R, 6S)-10-43)

[Chem. 53]

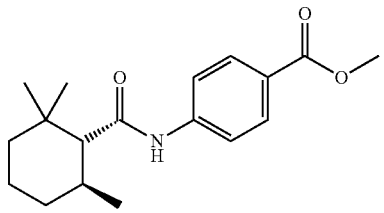

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then methyl 4-aminobenzoate (1.07 g, 1.20 eq.) was added thereto and was allowed to react with them for one and a half hours at 50° C. in an oil bath. The reaction solution was diluted with ethyl acetate (15 mL), and then water (5 mL) and a saturated aqueous solution of ammonium chloride (10 mL) were slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and isolation and purification were performed by silica gel column chromatography (hexane/ ethyl acetate), thereby obtaining a target compound (0.94 g, yield 53%) as a pale yellow solid.

Melting Point: 94° C. to 97° C.

HRMS: Mass 304.1907 Actual Measurement Value 304.1914 ([M+H]$^+$)

$^1$H-NMR (500 MHz, CDCl$_3$): δ 0.91 (d, 3H, J=6.4 Hz), 0.92-1.01 (m, 1H), 1.03 (s, 3H), 1.07 (s, 3H), 1.14-1.24 (m, 1H), 1.42-1.49 (m, 2H), 1.52-1.59 (m, 2H), 1.61 (d, 1H, J=11.1 Hz), 1.75-1.83 (m, 1H), 1.94-2.02 (m, 1H), 3.89 (s, 3H), 7.32 (br, 1H), 7.57-7.64 (m, 2H), 7.96-8.02 (m, 2H).

Example 31

Synthesis of (1R, 6S)-2,2,6-trimethyl-N-(4-(methylthio) phenyl) cyclohexane-1-carboxamide (Exemplary Compound (1R, 6S)-10-45)

[Chem. 54]

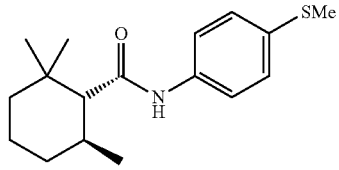

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 15 minutes at room temperature, and then 4-(methylthio) aniline (0.86 mL, 1.20 eq.) was added thereto and was allowed to react with them for two hours at 50° C. in an oil bath. The reaction solution was diluted with ethyl acetate (20 mL), and then 2N hydrochloric acid (15 mL) was slowly added thereto as a post-treatment. The oil layer was washed twice with a saturated aqueous solution of sodium bicarbonate (15 mL), and further washed once with a saturated saline solution (10 mL), followed by drying with sodium sulfate. The obtained solution was concentrated under reduced pressure, and recrystallized with hexane/ethyl acetate, thereby obtaining a target compound (0.67g, yield 39%) as a pale yellow crystal.

Melting Point: 157° C. to 159° C.

HRMS: Mass 292.1730 Actual Measurement Value 292.1734 ([M+H]$^+$)

$^1$H-NMR (500 MHz, CDCl$_3$): δ 0.91 (d, 3H, J=6.4 Hz), 0.92-1.00 (m, 1H), 1.02 (s, 3H), 1.07 (s, 3H), 1.18 (dt, 1H, J=5.7, 13.0 Hz), 1.42-1.47 (m, 1H), 1.50-1.59 (m, 3H), 1.74-1.82 (m, 1H), 1.92-2.00 (m, 1H), 2.46 (s, 3H), 7.09 (br, 1H), 7.24 (dt, 2H, J=2.7, 8.7 Hz), 7.46 (dt, 2H, J=2.1, 8.7 Hz).

Example 32

Synthesis of (1R, 6S)-N-(4-(cyanomethyl) phenyl)-2,2,6-trimethylcyclohexane-1-carboxamide (Exemplary Compound (1R, 6S)-10-49)

[Chem. 55]

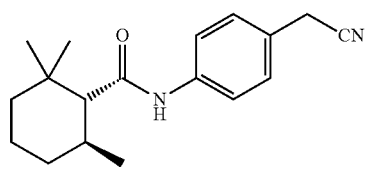

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath, and methanesulfonyl chloride (0.55 mL, 1.20 eq.) was slowly dropped therein. The mixture was stirred for 20 minutes at room temperature, and then 4-aminobenzyl cyanide (0.93 g, 1.20 eq.) was added thereto and was allowed to react with them for three hours at 40° C. in an oil bath. The reaction solution was diluted with ethyl acetate (10 mL), and then 2N hydrochloric acid (15 mL) was slowly added thereto as a post-treatment. The oil layer was washed once with 1N hydrochloric acid (20 mL), washed twice with a saturated aqueous solution of sodium bicarbonate (15 mL), and washed once with a saturated saline solution (10 mL), followed by drying with sodium sulfate. The obtained solution was concentrated under reduced pressure, and recrystallized with hexane/ethyl acetate, thereby obtaining a target compound (0.66 g, yield 40%) as a white solid.

Melting Point: 190° C. to 193° C.

HRMS: Mass 284.1848 Actual Measurement Value 284.1838 ([M]$^+$)

$^1$H-NMR (500 MHz, CDCl$_3$): δ 0.91 (d, 3H, J=6.4 Hz), 0.93-1.00 (m, 1H), 1.04 (s, 3H), 1.07 (s, 3H), 1.19 (dt, 1H, J=5.1, 12.8 Hz), 1.41-1.47 (m, 3H), 1.51-1.61 (m, 3H), 1.76-1.83 (m, 1H), 1.92-2.01 (m, 1H), 3.71 (s, 2H), 7.29 (br, 1H), 7.25-7.28 (m, 2H), 7.52-7.58 (m, 2H).

Example 33

Synthesis of (1R, 6S)-2,2,6-trimethyl-N-(pyridin-4-yl) cyclohexane-1-carboxamide (Exemplary Compound (1R, 6S)-10-51)

[Chem. 56]

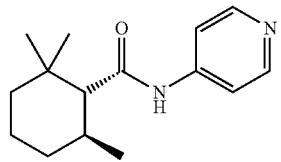

(1R, 6S)-2,2,6-trimethylcyclohexanecarboxylic acid ((1R, 6S)-5) (1.00 g, 5.87 mmol) which was obtained according to the method described in PTL 29, triethylamine (1.95 mL, 2.40 eq.), and acetonitrile (10 mL) were added to a 50 mL two neck flask under a nitrogen atmosphere. The temperature of the inside of the system was lowered to 0° C. to 5° C. by an ice bath and methanesulfonyl chloride (0.55 mL, 1.20 eq.) was dropped therein. The mixture was stirred for 20 minutes at room temperature, and then 4-aminopyridine (0.67 g, 1.20 eq.) was added thereto and was allowed to react with them for one hour at room temperature. The reaction solution was diluted with ethyl acetate (20 mL), and then a saturated aqueous solution of ammonium chloride (15 mL) was slowly added thereto as a post-treatment. The oil layer was washed once with a saturated aqueous solution of ammonium chloride (15 mL), washed twice with a saturated aqueous solution of sodium bicarbonate (15 mL), and washed once with a saturated saline solution (10 mL), followed by drying with sodium sulfate. The obtained solution was concentrated under reduced pressure, and isolation and purification were performed by silica gel column chromatography (hexane/ethyl acetate), thereby obtaining a target compound (0.45 g, yield 32%) as a white solid.

Melting Point: 64° C. to 68° C.

HRMS: Mass 247.1805 Actual Measurement Value 247.1807 ([M+H]$^+$)

$^1$H-NMR (500 MHz, CDCl$_3$): δ 0.87 (d, 3H, J=6.4 Hz), 0.83-0.90 (m, 1H), 1.00 (s, 3H), 1.05 (s, 3H), 1.11 (dt, 1H, J=5.5, 12.9 Hz), 1.36-1.43 (m, 1H), 1.45-1.54 (m, 2H), 1.72 (d, 1H, J=11.1 Hz), 1.68-1.78 (m, 1H), 1.88-2.00 (m, 1H), 7.52-7.58 (m, 2H), 8.39-8.44 (m, 2H), 8.70 (br, 1H).

Example 34

Synthesis of 2-hydroxy-2-phenylethyl (1R, 6S)-2,2,6-trimethylcyclohexane-1-carboxylate (Exemplary Compound (1R, 6S)-13-4)

[Chem. 57]

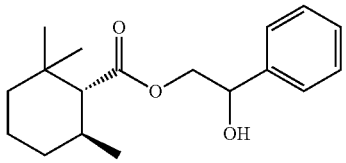

Phenethyldiol (8.29 g, 1.20 eq.) was placed in a 200 mL two neck flask under a nitrogen atmosphere, and toluene (100 mL) was added thereto, followed by performing stirring at room temperature, and then pyridine (5.2 mL, 1.30 eq.) and N,N-dimethylaminopyridine (0.31 g, 0.05 eq.) were added thereto. Further, thionyl chloride (3.97 mL, 1.10 eq.) was dropped in a solution obtained by mixing (1R, 6S)-2,2,6-trimethylcyclohexanecarboxylic acid ((1R, 6S)-5) (8.51 g, 50.0 mmol) obtained according to the method described in PTL 29 and N,N-dimethylformamide (20 mg) in toluene (50 mL). They were allowed to react for three hours at 100° C., and completion of the reaction was confirmed. After the temperature was lowered to room temperature and the reaction solution was diluted with toluene, 2N hydrochloric acid was slowly added thereto as a post-treatment. The oil layer was washed twice with a saturated aqueous solution of sodium bicarbonate, and further washed once with a saturated saline solution, followed by drying with sodium sulfate. The obtained solution was concentrated under reduced pressure, and purification was performed by silica gel column chromatography, thereby obtaining a target compound (6.39 g, yield 44%) as viscous oil.

HRMS: Mass 290.4030 Actual Measurement Value 290.4011 ([M+H]$^+$)

$^1$H-NMR (500 MHz, CDCl$_3$): δ 7.42-7.28 (m, 5H), 4.96 (brd, J=8 Hz, 1H), 4.31 (ddd, J=3.6, 9.2, 12.0 Hz, 1H), 4.19 (ddd, J=8.0, 10.4, 11.6 Hz, 1H), 2.57 (brs, 1H), 1.89-1.82 (m, 2H), 1.73 (ddd, J=1.2, 3.2, 14.0 Hz, 1H), 1.51 (tt, J=3.2, 10.0 Hz, 2H), 1.41 (dtd, J=1.2, 3.2, 13.2 Hz, 1H), 1.20-1.13 (m, 1H), 0.96 (d, J=2.4 Hz, 3H), 0.93 (s, 3H), 0.88 (ddd, J=3.4, 6.8, 16.0 Hz, 1H), 0.81 (dd, J=1.8, 5.8 Hz, 3H).

$^{13}$C-NMR (125 MHz, CDCl$_3$): δ 174.83, 139.87, 128.51×2, 128.12, 126.13×2, 72.53, 68.78, 68.71, 60.78, 41.09, 34.42, 33.33, 31.28, 31.27, 30.20, 30.17, 21.68, 21.56, 21.12, 21.06, 20.86, 20.84.

Example 35

Synthesis of (R)-2-hydroxy-2-phenylethyl (1R, 6S)-2,2,6-trimethylcyclohexane-1-carboxylate (exemplary compound (1R, 6S)-13-4-(R)) and (S)-2-hydroxy-2-phenylethyl (1R, 6S)-2,2,6-trimethylcyclohexane-1-carboxylate (Exemplary Compound (1R, 6S)-13-4-(S))

[Chem. 58]

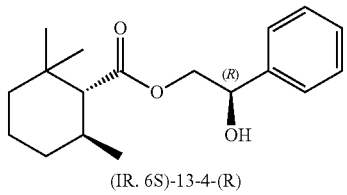

(1R, 6S)-13-4-(R)

[Chem. 59]

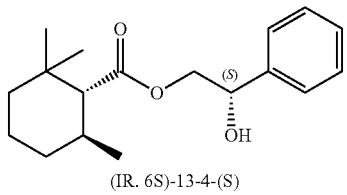

(1R, 6S)-13-4-(S)

An exemplary compound (1R, 6S)-13-4-(R) (2.47 g, yield 43%) was obtained as viscous oil from (1R, 6S)-2,2,6-trimethylcyclohexanecarboxylic acid ((1R, 6S)-5) (3.41 g, 20.0 mmol) and (R)-phenylethane-1,2-diol (2.90 g, 1.05 eq.) by the same method as that of Example 34.

An exemplary compound (1R, 6S)-13-4-(S) (2.46 g, yield 42%) was obtained as viscous oil from (1R, 6S)-2,2,6-trimethylcyclohexanecarboxylic acid ((1R, 6S)-5) (3.41 g, 20.0 mmol) and (S)-phenylethane-1,2-diol (2.90 g, 1.05 eq.) by the same method as that of Example 34.

Exemplary Compound (1R, 6S)-13-4-(R)

HRMS: Mass 290.4030 Actual Measurement Value 290.4073 ([M+H]$^+$)

$^1$H-NMR (500 MHz, CDCl$_3$): δ 7.40-7.28 (m, 5H), 4.32 (ddd, J=3.6, 9.2, 12.0 Hz, 1H), 4.17 (ddd, J=8.0, 10.4, 11.6 Hz, 1H), 2.57 (brs, 1H), 1.89-1.82 (m, 2H), 1.72 (ddd, J=1.2, 3.2, 14.0 Hz, 1H), 1.51 (tt, J=3.2, 10.0 Hz, 2H), 1.41 (dtd, J=1.2, 3.2, 13.2 Hz, 1H), 1.20-1.13 (m, 1H), 0.96 (d, J=2.4 Hz, 3H), 0.93 (s, 3H), 0.88 (ddd, J=3.4, 6.8, 16.0 Hz, 1H), 0.81 (dd, J=1.8, 5.8 Hz, 3H).

$^{13}$C-NMR (125 MHz, CDCl$_3$): δ 174.81, 139.84, 128.53×2, 128.12, 126.13×2, 72.57, 68.81, 60.81, 41.11, 34.44, 33.35, 31.30, 30.21, 21.61, 21.08, 20.86.

Exemplary Compound (1R, 6S)-13-4-(S)

HRMS: Mass 290.4030 Actual Measurement Value 290.4058 ([M+H]$^+$)

$^1$H-NMR (500 MHz, CDCl$_3$): δ 7.40-7.28 (m, 5H), 4.96 (brd, J=8 Hz, 1H), 4.30 (ddd, J=3.6, 9.2, 12.0 Hz, 1H), 4.19 (ddd, J=8.0, 10.4, 11.6 Hz, 1H), 2.57 (brs, 1H), 1.89-1.82 (m, 2H), 1.73 (ddd, J=1.2, 3.2, 14.0 Hz, 1H), 1.51 (tt, J=3.2, 10.0 Hz, 2H), 1.41 (dtd, J=1.2, 3.2, 13.2 Hz, 1H), 1.20-1.13 (m, 1H), 0.96 (d, J=2.4 Hz, 3H), 0.93 (s, 3H), 0.88 (ddd, J=3.4, 6.8, 16.0 Hz, 1H), 0.81 (dd, J=1.8, 5.8 Hz, 3H).

$^{13}$C-NMR (125 MHz, CDCl$_3$): δ 174.74, 139.87, 128.53×2, 128.12, 126.15×2, 72.55, 68.73, 60.80, 41.11, 34.43, 33.35, 31.28, 30.19, 21.60, 21.12, 20.87.

Synthesis Example 1

Synthesis of 4-methoxy-N-phenethylaniline (Secondary Amine Represented by Following Structural Formula)

[Chem. 60]

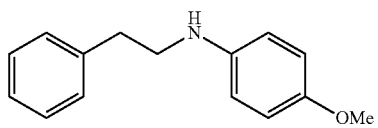

Bis(palladium)dibenzylideneacetone (71 mg, 1 mol %), dicyclohexyl (1-diphenyl-1-propen-2-yl) phosphine ligand (97 mg, 4 mol %) and toluene (20 mL) were added under a nitrogen atmosphere, and stirred at room temperature for one hour. Subsequently, phenethylamine (1.00 g, 7.80 mmol), bromoanisole (0.97 ml, 1.0 eq.), and sodium-tert-butoxide (0.90 g, 1.2 eq.) were added thereto, and the mixture was heated and stirred at 100° C. for five hours. The temperature of the reaction solution was lowered to room temperature, and then extraction and washing with ethyl acetate/water were performed. The oil layer was dried by anhydrous magnesium sulfate, and the residue obtained by filtration and concentration was isolated and purified by silica gel column chromatography, thereby obtaining a target compound (1.05 g, yield 59%) as pale yellow oil.

$^1$H-NMR (500 MHz, CDCl$_3$): δ 2.90 (t, 2H, J=7.0 Hz), 3.36 (t, 2H, J=7.1 Hz), 3.75 (s, 3H), 6.57-6.61 (m, 2H), 6.75-6.80 (m, 2H), 7.20-7.37 (n, 6H).

Example 36

Evaluation of Cooling Intensity (TRPM8 Activity Evaluation)

It is common that a compound having a cooling effect such as menthol generally induces a cool-feeling by activating melastatin transient receptor potential channel 8 (TRPM8) as a cold stimulation receptor (for example, see Non-Patent Literature 3). Therefore, in order to evaluate the cooling intensity, EC$_{50}$ values of each of the compounds obtained in Examples and comparative compounds (N,2,2,6-tetramethylcyclohexanecarboxamide synthesized according to the method described in PTL 29, 1-menthol, WS-3, WS-5 and WS-23) in TRPM8 activation actions were measured in accordance with the following procedures.

WS-3, WS-5 and WS-23 are compounds shown in Table 6 below.

(1) Preparation of Human TRPM8 Stable Expression Cell Line

The full-length human TRPM8 gene was amplified from plasmid RC220615 (manufactured by Origene) using a PCR method. The obtained PCR product was subcloned into pcDNA5/FRT/TO (manufactured by Thermo Fisher Scientific K.K.), and then it was introduced into Flp-In293293 cells (manufactured by Thermo Fisher Scientific K.K.) by using a Flp-InT-REx system (manufactured by Thermo Fisher Scientific K.K.), so that a human TRPM8 stable expression cell line was prepared.

(2) Evaluation of Human TRPM8 Activity

The cultured human TRPM8 stable expression cells were seeded at a ratio of 50,000 cells/well to a poly-D-lysine-coated 96-well microplate (manufactured by Corning Incorporated), 1 μg/mL of doxycycline (manufactured by Takara Bio Inc.) was added thereto, and then the seeded cells were cultured at 37° C. for one night, so that the expression of the human TRPM8 was induced.

The culture solution was replaced with a buffer solution, and then, a fluorescent calcium indicator (Fluo4-AM: manufactured by Dojindo Laboratories) was added thereto, the cells were incubated at 37° C. for 30 minutes, and they were transferred to a fluorescent microplate reader (FlexStation3: manufactured by Molecular Devices, LLC.). Each of the compounds obtained in Examples and comparative compounds was added in a final concentration range of 0.1 μM to 1000 μM, and the changes in fluorescence having a wavelength of 525 nm when excited at a wavelength of 485 nm were measured at a device temperature of 32° C., and then EC$_{50}$ values were determined.

EC$_{50}$ values of the compounds obtained in Examples and comparative compounds in TRPM8 activation actions were shown in the following Tables 1 to 6.

TABLE 1

| Compound in Examples | EC$_{50}$ (μM) |
|---|---|
| (1R, 6S)-10-1 | 0.59 |
| (1R, 6S)-10-4 | 0.60 |
| (1S, 6R)-10-4 | 6.36 |
| (1R, 6S)-10-5 | 3.96 |

TABLE 1-continued

| Compound in Examples | EC$_{50}$ (μM) |
|---|---|
| (1S, 6R)-10-5 | 7.68 |
| (1R, 6S)-10-6 | 0.55 |
| (1S, 6R)-10-6 | 5.98 |

TABLE 2

| Compound in Examples | EC$_{50}$ (μM) |
|---|---|
| (1R, 6S)-10-8 | 1.19 |
| (1S, 6R)-10-8 | 5.90 |
| (1R)-10-10 | 1.11 |

TABLE 2-continued

| Compound in Examples | EC$_{50}$ (μM) |
|---|---|
| (1S)-10-11 | 2.10 |
| (1R, 6S)-10-12 | 9.44 |
| (1R, 6S)-10-13 | 2.00 |
| (1R, 6S)-10-14 | 2.55 |
| (1R, 6S)-10-15 | 7.72 |

TABLE 3

| Compound in Examples | EC$_{50}$ (μM) |
|---|---|
| (1R, 6S)-10-19 | 2.76 |

TABLE 3-continued
| Compound in Examples | EC$_{50}$ (μM) |
|---|---|
| 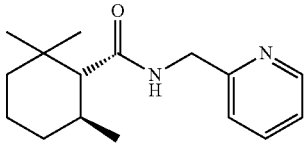 (1R, 6S)-10-22 | 29.8 |
| 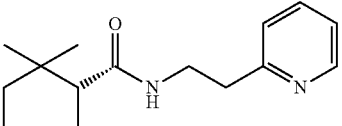 (1R, 6S)-10-23 | 4.84 |
| 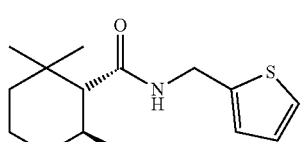 (1R, 6S)-10-26 | 1.97 |
| 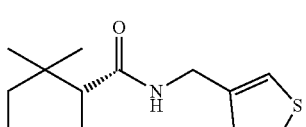 (1R, 6S)-10-27 | 3.48 |
| 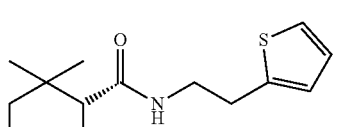 (1R, 6S)-10-28 | 0.85 |
| 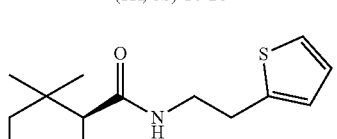 (1S, 6R)-10-28 | 3.08 |
TABLE 4
| Compound in Examples | EC$_{50}$ (μM) |
|---|---|
| 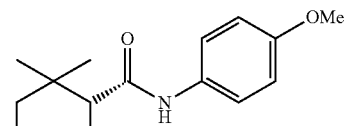 (1R, 6S)-10-33 | 6.14 |
TABLE 4-continued
| Compound in Examples | EC$_{50}$ (μM) |
|---|---|
| 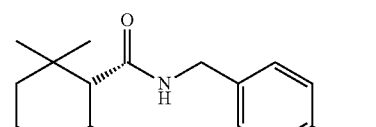 (1R, 6S)-10-35 | 1.59 |
| 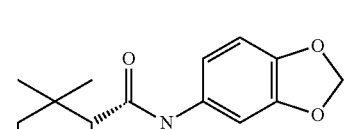 (1R, 6S)-10-36 | 2.42 |
| 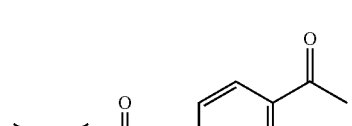 (1R, 6S)-10-38 | 3.75 |
| 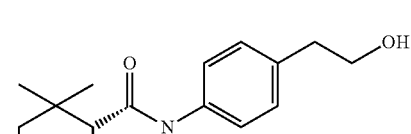 (1R, 6S)-10-41 | 1.19 |
| 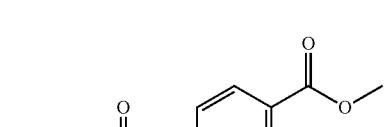 (1R, 6S)-10-42 | 1.67 |
| 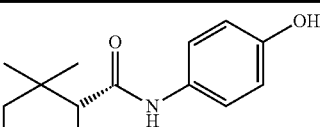 (1R, 6S)-10-43 | 5.76 |

TABLE 5

| Compound in Examples | EC$_{50}$ (μM) |
|---|---|
| 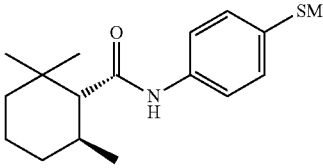 (1R, 6S)-10-45 | 1.06 |
| 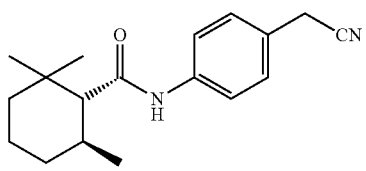 (1R, 6S)-10-49 | 1.77 |
| 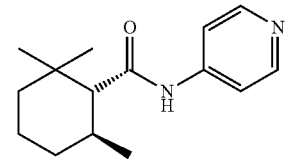 (1R, 6S)-10-51 | 15.0 |
| 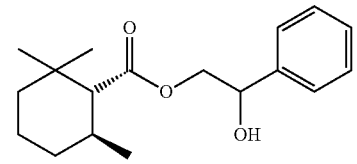 (1R, 6S)-13-4 | 3.07 |
| 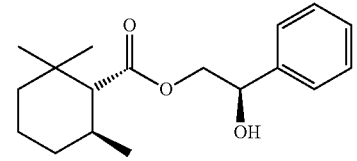 (1R, 6S)-13-4-(R) | 1.78 |
| 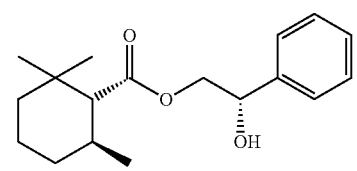 (1R, 6S)-13-4-(S) | 1.74 |

TABLE 6

| Comparative compound | EC$_{50}$ (μM) |
|---|---|
| 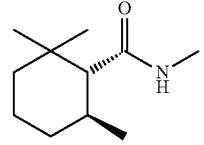 N,2,2,6-tetramethylcyclo-hexanecarboxamide | 110 |
| 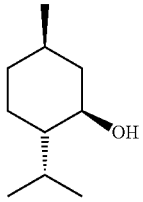 l-menthol | 4.34 |
| 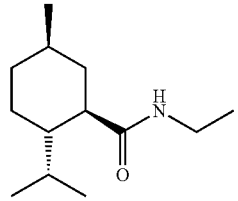 WS-3 | 1.61 |
| 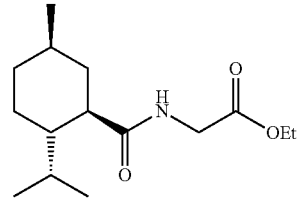 WS-5 | 0.73 |
| 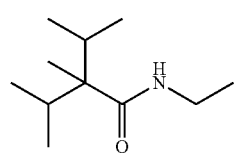 WS-23 | 23.1 |

As shown in the above Tables 1 to 5, each of the compounds obtained in Examples had TRPM8 activation action much more excellent than that of N,2,2,6-tetramethylcyclohexanecarboxamide shown in Table 6. Therefore, the compounds obtained in the Examples have a cooling effect much stronger than that of N,2,2,6-tetramethylcyclohexanecarboxamide.

Further, as shown in Tables 1 to 5, each of the compounds obtained in Examples shows a strong cooling effect equal to or stronger than the existing cooling agents such as l-menthol, WS-3, WS-5 and WS-23 shown in Table 6.

Example 37

A 30 ppm aqueous solution of the exemplary compound ((1R, 6S)-10-1) and a 30 ppm aqueous solution of the comparative compound (N,2,2,6-tetramethylcyclohexanecarboxamide, 1-menthol, WS-3, and WS-5) were prepared, and the aqueous solutions were used to perform the evaluation.

The evaluation was performed by four flavorists. The aqueous solution was taken into the mouth and spat out after the mouth was rinsed, and cooling intensity, cool-feeling persistence, and quality of a cool-feeling in the oral cavity were evaluated.

Cooling intensity of the exemplary compound ((1R, 6S)-10-1) was very strong, and was apparently stronger than that of the comparative compounds (N,2,2,6-tetramethylcyclohexanecarboxamide, 1-menthol, and WS-3). In addition, the cool-feeling lasted for 30 minutes or longer.

The cooling intensity of the exemplary compound ((1R, 6S)-10-1) was stronger than that of WS-5, and the cool-feeling lasted for 30 minutes or longer.

Regarding the quality of the cool-feeling, the exemplary compound ((1R, 6S)-10-1) had almost the same tingling sensation as WS-5.

Example 38

Toothpaste Scenting Evaluation

Toothpaste (A) to (C) was prepared in accordance with the following formulations.

(A) toothpaste base 990.0 g+toothpaste flavor BASE 4.0 g+1-menthol 3.0 g+ethyl alcohol (EtOH) 3.0 g (B) toothpaste base 990.0 g+toothpaste flavor BASE 4.0 g+1-menthol 3.0 g+comparative compound (WS-5) (1 mass % in EtOH) 3.0 g (C) toothpaste base 990.0 g+toothpaste flavor BASE 4.0 g+1-menthol 3.0 g+exemplary compound ((1R, 6S)-10-1) (1 mass % in EtOH) 3.0 g

[Chem. 61]

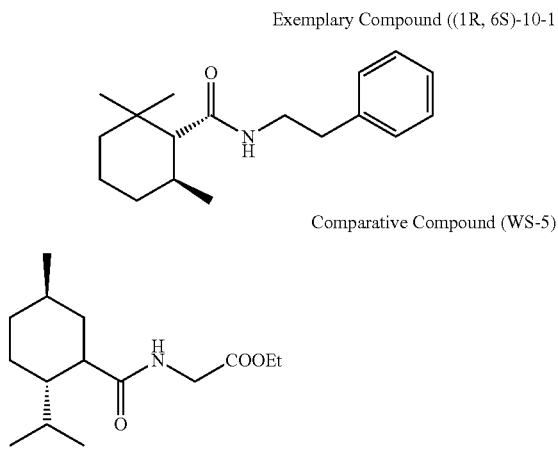

Exemplary Compound ((1R, 6S)-10-1

Comparative Compound (WS-5)

The prescription for the toothpaste flavor BASE is as follows.

TABLE 7

| (Component) | (Blending Amount g) |
|---|---|
| Anethole | 0.6 |
| Eucalyptol | 0.2 |
| Lemon oil | 0.1 |

TABLE 7-continued

| (Component) | (Blending Amount g) |
|---|---|
| Mentha white oil | 1.0 |
| Peppermint oil | 1.5 |
| Propylene Glycol (PG) | 0.6 |
| Total Amount | 4.0 |

The prescription for the toothpaste base is as follows.

TABLE 8

| (Component) | (Blending Amount g) |
|---|---|
| Calcium carbonate | 400.0 |
| Silicic anhydride | 16.5 |
| Sorbitol solution (70 mass %) | 240.0 |
| Sodium lauryl sulfate | 13.0 |
| Sodium carboxymethyl cellulose | 12.5 |
| Carrageenan | 3.0 |
| Sodium benzoate | 4.0 |
| Sodium saccharin | 1.5 |
| Purified water | 259.5 |
| Propylene Glycol (PG) | 40.0 |
| Total Amount | 990.0 |

[Evaluation]

The evaluation was performed by three flavorists. The above three flavorists placed about 1 g of toothpaste on a toothbrush separately, and brushed the teeth for about five minutes in a usual brushing manner. The above three flavorists brushed the teeth and then rinsed the mouth, and then intensity, persistence, and quality of a cool-feeling in the oral cavity were evaluated.

According to the evaluation based on the above three flavorists, the toothpaste (B) and toothpaste (C) had cooling effects stronger than that of toothpaste (A), and the toothpaste (C) had a cooling effect equal to or stronger than that of the toothpaste (B).

In addition, the toothpaste (C) exhibited an equivalent flavor profile of the toothpaste flavor BASE, and stimulation other than the sense of cooling thereof was hardly felt, as compared with the toothpaste (B). Both the toothpaste (B) and the toothpaste (C) exhibited a cool-feeling for 30 minutes or longer.

Example 39

Mouthwash Scenting Evaluation

Mouthwashes (D) to (F) were prepared in accordance with the following formulations.

(D) mouthwash base 999.0 g+mouthwash flavor BASE 0.35 g+1-menthol 0.35 g+ethyl alcohol (EtOH) 0.3 g (E) mouthwash base 999.0 g+mouthwash flavor BASE 0.35 g+I-menthol 0.35 g+comparative compound (WS-5) (10 mass % in EtOH) 0.3 g (F) mouthwash base 999.0 g+mouthwash flavor BASE 0.35 g+I-menthol 0.35 g+exemplary compound ((1R, 6S)-10-1) (10 mass % in EtOH) 0.3 g

[Chem. 62]

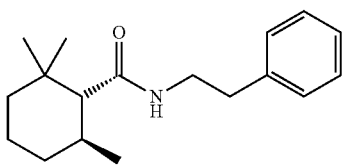

Exemplary Compound (IR. 6S)-10-1

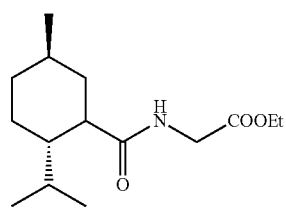

Comparative Compound (WS-5)

The prescription for the mouthwash flavor BASE is as follows.

TABLE 9

| (Component) | (Blending Amount g) |
| --- | --- |
| Anethole | 0.02 |
| 1-carvone | 0.01 |
| Mentha white oil | 0.05 |
| Peppermint oil | 0.20 |
| Propylene Glycol (PG) | 0.07 |
| Total Amount | 0.35 |

The prescription for the mouthwash base is as follows.

TABLE 10

| (Component) | (Blending Amount g) |
| --- | --- |
| Refined glycerin | 100.0 |
| Polyoxyethylene cured castor oil 60 | 10.0 |
| Sodium benzoate | 0.5 |
| Sodium saccharin | 0.1 |
| Purified water | 838.4 |
| Ethyl alcohol 95 mass % | 50.0 |
| Total Amount | 999.0 |

[Evaluation]

The evaluation was performed by three flavorists. The above three flavorists took 20 mL of mouthwashes into the mouth and spat out the mouthwashes after rinsing the mouth, and intensity, persistence, and quality of a cool-feeling in the oral cavity were evaluated.

According to the evaluation based on the above three flavorists, the mouthwash (E) and a mouthwash (F) had cooling effects stronger than that of the mouthwash (D), and the mouthwash (F) had a cooling effect equal to or stronger than the mouthwash (E).

In addition, the mouthwash (F) exhibited an equivalent mint flavor profile of the mouthwash flavor BASE, and stimulation other than the sense of cooling thereof was hardly felt, as compared with the mouthwash (E). Both the mouthwash (E) and the mouthwash (F) exhibited a cool-feeling for 30 minutes or longer.

Example 40

Chewing Gum Scenting Evaluation

Chewing gums (G) to (I) were prepared in accordance with the following formulations.

(G) chewing gum base 990.0 g+peppermint flavor BASE 6.3 g+1-menthol 0.7 g+ethyl alcohol (EtOH) 3.0 g (H) chewing gum base 990.0 g+peppermint flavor BASE 6.3 g+1-menthol 0.7 g+comparative compound (WS-5) (1 mass % in EtOH) 3.0 g (I) chewing gum base 990.0 g+peppermint flavor BASE 6.3 g+1-menthol 0.7 g+exemplary compound ((1R, 65)-10-1) (1 mass % in EtOH) 3.0 g

[Chem. 63]

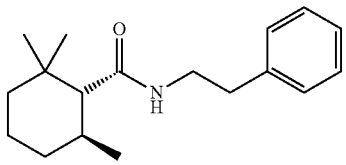

Exemplary Compound ((IR. 6S)-10-1

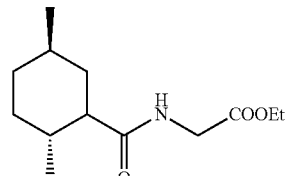

Comparative Compound (WS-5)

The prescription for the peppermint flavor BASE is as follows.

TABLE 11

| (Component) | (Blending Amount g) |
| --- | --- |
| Eucalyptol | 0.3 |
| Mentha white oil | 2.5 |
| Peppermint oil | 3.5 |
| Total Amount | 6.3 |

The prescription for the chewing gum base is as follows.

TABLE 12

| (Component) | (Blending Amount g) |
| --- | --- |
| Xylitol | 320.0 |
| Maltitol | 338.8 |
| Gum base | 280.0 |
| Reduced starch saccharide (BRIX70) | 40.0 |
| Glycerin | 10.0 |
| Acesulfame K | 0.6 |
| Aspartame | 0.6 |
| Total Amount | 990.0 |

[Evaluation]

The evaluation was performed by three flavorists. The above three flavorists took 1 g of chewing gum into the mouth, chewed the chewing gum about five minutes and spat it out. Intensity, persistence, and quality of a cool-feeling in the oral cavity were evaluated by the above three flavorists.

According to the evaluation based on the above three flavorists, the chewing gum (H) and chewing gum (I) had a cooling effect stronger than that of the chewing gum (G), and the chewing gum (I) had a cooling effect equal to or stronger than that of the chewing gum (H).

In addition, the chewing gum (I) exhibited a somewhat sharp cool-feeling from the beginning of chewing when it was chewed, a well-ventilated cool-feeling spread in the oral cavity, and no harshness or other stimuli was felt. In addition, a cool-feeling was felt for 30 minutes or longer after the chewing gum (I) was spat out.

Example 41

Candy Scenting Evaluation

Candies (J) to (L) having the following formulations were prepared in accordance with the following production method.

(J) candy base 998.0 g+herb flavor BASE 0.9 g+1-menthol 0.8 g+ethyl alcohol (EtOH) 0.3 g (K) candy base 998.0 g +herb flavor BASE 0.9 g+1-menthol 0.8 g+comparative compound (WS-5) (10 mass % in EtOH) 0.3 g (L) candy base 998.0 g+herb flavor BASE 0.9 g+1-menthol 0.8 g+exemplary compound ((1R, 6S)-10-1) (10 mass % in EtOH) 0.3 g

[Chem. 64]

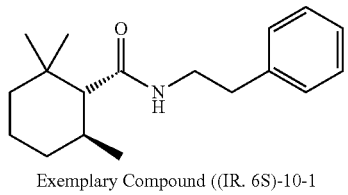

Exemplary Compound ((IR. 6S)-10-1

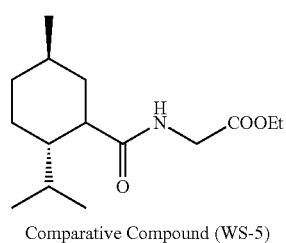

Comparative Compound (WS-5)

The prescription for the herb flavor BASE is as follows.

TABLE 13

| (Component) | (Blending Amount g) |
| --- | --- |
| Star anise oil | 0.100 |
| Eucalyptol | 0.276 |
| Eucalyptus oil | 0.520 |
| Sage oil | 0.004 |
| Total Amount | 0.900 |

The prescription for the candy base is as follows.

TABLE 14

| (Component) | (Blending Amount g) |
| --- | --- |
| Granulated sugar | 500.0 g |
| Starch syrup (BRIX 85, 47DE) | 430.0 g |
| Purified water | 170.0 g |
| Total Amount | 1100.0 g |

[Method of Preparing Candy]

998.0 g of 1100.0 g of the candy base of the above prescription was heated to 150° C. Then, the fire was extinguished, dough was weighted, and materials other than the candy bases shown in the above (J) to (L) were respectively mixed therewith. The mixture flowed to a mold and was molded while the temperature thereof was maintained at 135° C. to 140° C. The mixture was removed from the mold after cooling, and candies (J) to (L) of about 3 g per grain were prepared.

[Evaluation]

The evaluation was performed by three flavorists. The above three flavorists took a grain of candy into the mouth and melt the candy by licking, and after the candy was completely disappeared, intensity, persistence, and quality of a cool-feeling in the oral cavity were evaluated.

According to the evaluation based on the above three flavorists, the candy (K) and candy (L) had a cooling effect stronger than that of the candy (J), and the candy (L) had a cooling effect equal to or stronger than that of the candy (K).

Further, the candy (L) exhibited a sharp refresh-feeling from the beginning of licking when it was licked, and after a while, the refresh-feeling became a refresh-feeling that stimulates the back of the throat, and no harshness or other stimuli was felt. In addition, a cool-feeling was felt for 30 minutes or longer after the candy (L) was completely disappeared.

Although the present invention is described in detail with reference to specific embodiments, it is apparent to those skilled in the art that various changes and modifications may be made without departing from the spirit and scope of the present invention. The present application is based on Japanese Patent Application No. 2017-200504 filed on Oct. 16, 2017, the contents of which are incorporated herein by reference.

The invention claimed is:

1. A cooling agent composition comprising a 2,2,6-trimethylcyclohexanecarboxylic acid derivative represented by the following general formula (1):

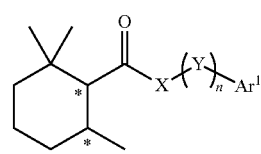

(1)

wherein the symbol * represents an asymmetric carbon atom,

X represents NH, N(ZAr$^2$), O or S, Z represents a single bond or an alkylene group having 1 to 3 carbon atoms which may have a substituent, Ar$^2$ represents an aryl group having 6 to 20 carbon atoms which may have a substituent or an aromatic heterocyclic group having 2 to 15 carbon atoms which may have a substituent, Y each independently represents a methylene group which may have a substituent, n represents an integer of 0 to 3, and $Ar^1$ represents an aryl group having 6 to 20 carbon atoms which may have a substituent or an aromatic heterocyclic group having 2 to 15 carbon atoms which may have a substituent.

2. The cooling agent composition according to claim 1, wherein X represents NH or $N(ZAr^2)$ in the 2,2,6-trimethylcyclohexanecarboxylic acid derivative.

3. The cooling agent composition according to claim 1, wherein X represents NH or $N(ZAr^2)$ in the 2,2,6-trimethylcyclohexanecarboxylic acid derivative, and the 2,2,6-trimethylcyclohexanecarboxylic acid derivative is a (1R, 6S)-form.

4. The cooling agent composition according to claim 1, wherein X represents NH or $N(ZAr^2)$, n represents 0 or 2, and Z represents a single bond or an ethylene group which may have a substituent in the 2,2,6-trimethylcyclohexanecarboxylic acid derivative.

5. The cooling agent composition according to claim 1, wherein X represents NH or $N(ZAr^2)$, n represents 0 or 2, and Z represents a single bond or an ethylene group which may have a substituent in the 2,2,6-trimethylcyclohexanecarboxylic acid derivative, and the 2,2,6-trimethylcyclohexanecarboxylic acid derivative is a (1R, 6S)-form.

6. The cooling agent composition according to claim 1, wherein X represents NH or $N(ZAr^2)$, n represents 2, and Z represents an ethylene group which may have a substituent, in the 2,2,6-trimethylcyclohexanecarboxylic acid derivative.

7. The cooling agent composition according to claim 1, wherein X represents NH or $N(ZAr^2)$, n represents 2, and Z represents an ethylene group which may have a substituent in the 2,2,6-trimethylcyclohexanecarboxylic acid derivative, and the 2,2,6-trimethylcyclohexanecarboxylic acid derivative is a (1R, 6S)-form.

8. A sensory stimulant composition comprising the cooling agent composition according to claim 1.

9. The sensory stimulant composition according to claim 8, further comprising at least one kind of warming substance.

10. The sensory stimulant composition according to claim 9, wherein the warming substance is at least one warming substance selected from the group consisting of:

one or more kinds of compounds selected from vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, bis-capsaicin, trishomocapsaicin, nornorcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more kinds of natural products selected from capsicum pepper oil, capsicum pepper oleoresin, ginger oleoresin, jambu oleoresin (extract from Spilanthes acmella L. var. oleracea Clarke), Japanese pepper extract, sanshoamide, black pepper extract, white pepper extract, and Polygonum extract.

11. The cooling agent composition according to claim 1, further comprising at least one kind of cooling substance other than the 2,2,6-trimethylcyclohexanecarboxylic acid derivative.

12. The cooling agent composition according to claim 11, wherein the cooling substance is at least one cooling substance selected from the group consisting of:

one or more kinds of compounds selected from menthol, menthone, camphor, pulegol, isopulegol, cineole, cubenol, menthyl acetate, pulegyl acetate, isopulegyl acetate, menthyl salicylate, pulegyl salicylate, i sopulegyl salicylate, 3 -(1-menthoxy)propane- 1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3 -carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3 -dimethylbutanamide, N-(1,1-dimethyl-2-hydroxyethyl)-2,2-dimethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p -menthoxy)ethoxy]ethanol, 2,6-diethyl-5-isopropyl-2-methyltetrahydropyran, and trans-4-tert-butylcyclohexanol;

one or more kinds of sugar alcohols selected from xylitol, erythritol, dextrose, and sorbitol; and one or more kinds of natural products selected from Japanese mint oil, peppermint oil, spearmint oil, and eucalyptus oil.

13. A flavor or fragrance composition comprising the sensory stimulant composition according claim 8.

14. The flavor or fragrance composition according to claim 13, wherein a content of the sensory stimulant composition is from 0.00001 mass % to 90 mass %.

15. A product comprising the flavor or fragrance composition according to claim 13, the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

16. The product according to claim 15, wherein a content of the flavor or fragrance composition is from 0.00001 mass % to 50 mass %.

17. A method for manufacturing a product, comprising blending a product with the flavor or fragrance composition according to claim 13, wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

18. A product comprising the sensory stimulant composition according to claim 8, the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

19. The product according to claim 18, wherein a content of the sensory stimulant composition is from 0.00001 mass % to 50 mass %.

20. A method for manufacturing a product, comprising blending a product with the sensory stimulant composition according to claim 8, wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, quasi-drugs and pharmaceuticals.

21. A 2,2,6-trimethylcyclohexanecarboxylic acid derivative represented by the following general formula (1-1):

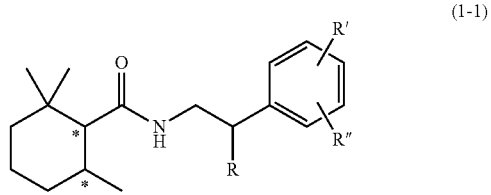

(1-1)

wherein the symbol * represents an asymmetric carbon atom, and R, R' and R" each independently represent a hydrogen atom, a hydroxy group, or a methoxy group.

22. A 2,2,6-trimethylcyclohexanecarboxylic acid derivative represented by the following structural formula (10-1):

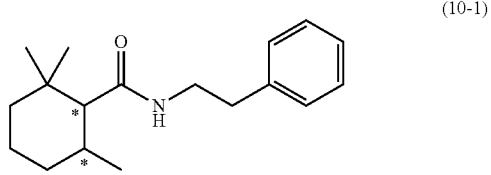 [SMILES: CC1CCCC(C)(C)C1C(=O)NCCc1ccccc1]

(10-1)

wherein the symbol * represents an asymmetric carbon atom.

* * * * *